United States Patent
Shuros et al.

(10) Patent No.: US 10,926,095 B2
(45) Date of Patent: Feb. 23, 2021

(54) SYSTEMS AND METHODS FOR CORRECTING CARDIAC CONDUCTION ABNORMALITY USING HIS-BUNDLE PACING

(71) Applicant: Cardiac Pacemakers, Inc., St. Paul, MN (US)

(72) Inventors: Allan Charles Shuros, St. Paul, MN (US); David Arthur Casavant, Reading, MA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 26 days.

(21) Appl. No.: 16/175,374

(22) Filed: Oct. 30, 2018

(65) Prior Publication Data

US 2019/0126040 A1 May 2, 2019

Related U.S. Application Data

(60) Provisional application No. 62/580,711, filed on Nov. 2, 2017, provisional application No. 62/595,535, filed (Continued)

(51) Int. Cl.
*A61N 1/368* (2006.01)
*A61N 1/37* (2006.01)
(Continued)

(52) U.S. Cl.
CPC ............ *A61N 1/368* (2013.01); *A61N 1/056* (2013.01); *A61N 1/362* (2013.01); *A61N 1/3684* (2013.01);
(Continued)

(58) Field of Classification Search
CPC .... A61N 1/056; A61N 1/362; A61N 1/36507; A61N 1/36521; A61N 1/36564;
(Continued)

(56) References Cited

U.S. PATENT DOCUMENTS 4,157,711 A * 6/1979 Yotam ................ A61B 5/04012
600/521
4,751,931 A * 6/1988 Briller .................. A61B 5/0428
600/509

(Continued)

OTHER PUBLICATIONS

Deshmukh, P., et al., "Permanent, Direct His-Bundle Pacing: A Novel Approach to Cardiac Pacing in Patients With Normal His-Purkinje Activation", Circulation, 101(8), (Feb. 29, 2000), 869-877.

(Continued)

*Primary Examiner* — Christopher A Flory
(74) *Attorney, Agent, or Firm* — Schwegman Lundberg & Woessner, P.A.

(57) ABSTRACT

Systems and methods for pacing cardiac conductive tissue are described. A medical system includes an electrostimulation circuit to generate His-bundle pacing (HBP) pulses for delivery at or near a His bundle of the heart. A control circuit may time the delivery of the HBP pulses within a tissue refractory period subsequent to an intrinsic His-bundle activation of a first His-bundle portion. Based on an evoked His-bundle activation of a second His-bundle portion, the system may determine whether correction of intra-Hisian block has occurred. The system additionally includes a threshold test circuit to determine an individualized pacing threshold representing minimal energy to excite the His bundle and to correct the cardiac conduction abnormality.

20 Claims, 5 Drawing Sheets

Related U.S. Application Data on Dec. 6, 2017, provisional application No. 62/595,541, filed on Dec. 6, 2017.

(51) Int. Cl.
    *A61N 1/05* (2006.01)
    *A61N 1/362* (2006.01)
    *A61N 1/365* (2006.01)
    *A61B 5/0452* (2006.01)

(52) U.S. Cl.
    CPC ..... *A61N 1/36507* (2013.01); *A61N 1/36521* (2013.01); *A61N 1/36564* (2013.01); *A61N 1/3712* (2013.01); *A61B 5/0452* (2013.01); *A61N 1/36578* (2013.01); *A61N 1/371* (2013.01); *A61N 1/3702* (2013.01)

(58) Field of Classification Search
    CPC .... A61N 1/368; A61N 1/3684; A61N 1/3712; A61B 5/0452
    See application file for complete search history.

(56) References Cited

U.S. PATENT DOCUMENTS

| | | | |
|---|---|---|---|
| 5,174,286 A | 12/1992 | Chirife | |
| 5,800,467 A | 9/1998 | Park et al. | |
| 6,718,206 B2 | 4/2004 | Casavant | |
| RE43,569 E * | 8/2012 | Olson | A61B 5/04011 600/450 |
| 8,565,880 B2 | 10/2013 | Dong et al. | |
| 8,588,907 B2 | 11/2013 | Arcot-Krishnamurthy et al. | |
| 8,688,234 B2 | 4/2014 | Ortega et al. | |
| 8,761,880 B2 | 6/2014 | Maskara et al. | |
| 8,954,147 B2 | 2/2015 | Arcot-Krishnamurthy et al. | |
| 2002/0138014 A1* | 9/2002 | Baura | A61B 5/726 600/526 |
| 2003/0120165 A1* | 6/2003 | Bjorling | A61N 1/3622 600/515 |
| 2004/0049235 A1 | 3/2004 | Deno et al. | |
| 2007/0016261 A1 | 1/2007 | Dong et al. | |
| 2007/0273504 A1* | 11/2007 | Tran | A61B 5/04012 340/539.12 |
| 2007/0276270 A1* | 11/2007 | Tran | A61B 5/002 600/508 |
| 2008/0001735 A1* | 1/2008 | Tran | G06F 19/00 340/539.22 |
| 2008/0004904 A1* | 1/2008 | Tran | A61B 5/0022 705/2 |
| 2009/0005830 A1 | 1/2009 | Zhu et al. | |
| 2009/0227876 A1* | 9/2009 | Tran | A61B 5/411 600/483 |
| 2009/0259272 A1* | 10/2009 | Reddy | A61N 1/0573 607/28 |
| 2009/0318779 A1* | 12/2009 | Tran | A61B 5/002 600/301 |
| 2011/0115624 A1* | 5/2011 | Tran | A61B 5/0008 340/540 |
| 2011/0181422 A1* | 7/2011 | Tran | A61B 5/0022 340/573.1 |
| 2011/0245702 A1* | 10/2011 | Clark | G01R 5/28 600/523 |
| 2011/0264158 A1* | 10/2011 | Dong | A61B 5/7264 607/9 |
| 2011/0319956 A1 | 12/2011 | Zhu et al. | |
| 2012/0004564 A1* | 1/2012 | Dobak, III | A61B 5/1102 600/510 |
| 2012/0092157 A1* | 4/2012 | Tran | A61B 5/0476 340/539.12 |
| 2012/0095352 A1* | 4/2012 | Tran | G06Q 30/0269 600/490 |
| 2012/0157822 A1* | 6/2012 | van Dam | A61B 5/0402 600/411 |
| 2012/0239106 A1* | 9/2012 | Maskara | A61N 1/371 607/28 |
| 2012/0283587 A1* | 11/2012 | Gosh | A61B 5/0402 600/510 |
| 2012/0284003 A1* | 11/2012 | Gosh | A61N 1/3684 703/2 |
| 2012/0330109 A1* | 12/2012 | Tran | A61B 5/681 600/301 |
| 2013/0009783 A1* | 1/2013 | Tran | A61B 5/0402 340/669 |
| 2013/0158621 A1* | 6/2013 | Ding | A61N 1/37 607/17 |
| 2013/0172691 A1* | 7/2013 | Tran | A61B 8/06 600/301 |
| 2013/0231574 A1* | 9/2013 | Tran | A61B 5/1112 600/479 |
| 2014/0107724 A1* | 4/2014 | Shuros | A61N 1/3712 607/28 |
| 2019/0022378 A1* | 1/2019 | Prillinger | A61N 1/3962 |

OTHER PUBLICATIONS

Huang, Weijian, et al., "Feasibility of His Bundle Pacing to Correct Left Bundle Branch Block in Heart Failure Patients", Journal of the American College of Cardiology, vol. 70, No. 16, Suppl C, 2017, GW28-1237, 1 page.

Teng, Alexandra E., "Physiological mechanisms of QRS narrowing in bundle branch block patients undergoing permanent His bundle pacing", Journal of Electrocardiology 49 (2016) 644-648.

"International Application U.S. Appl. No. PCT/US2018/058140, International Preliminary Report on Patentability dated May 14, 2020", 8 pgs.

"International Application U.S. Appl. No. PCT/US2018/058140, International Search Report dated Dec. 12, 2018", 5 pgs.

"International Application U.S. Appl. No. PCT/US2018/058140, Written Opinion dated Dec. 12 2018", 6 pgs.

* cited by examiner

SYSTEMS AND METHODS FOR CORRECTING CARDIAC CONDUCTION ABNORMALITY USING HIS-BUNDLE PACING

CLAIM OF PRIORITY

This application claims the benefit of priority under 35 U.S.C. § 119(e) of U.S. Provisional Patent Application Ser. No. 62/580,711, filed on Nov. 2, 2017, U.S. Provisional Patent Application Ser. No. 62/595,535, filed on Dec. 6, 2017, and U.S. Provisional Patent Application Ser. No. 62/595,541, filed on Dec. 6, 2017, each of which is herein incorporated by reference in its entirety.

TECHNICAL FIELD

This document relates generally to medical systems, and more particularly, to systems, devices and methods for pacing of cardiac conductive tissue, such as a His bundle.

BACKGROUND

The heart is the center of a person's circulatory system. It includes an electro-mechanical system performing two major pumping functions. The left portions of the heart, including the left atrium (LA) and left ventricle (LV), draw oxygenated blood from the lungs and pump it to the organs of the body to provide the organs with their metabolic needs. The right portions of the heart, including the right atrium (RA) and right ventricle (RV), draw deoxygenated blood from the body organs and pump it to the lungs where the blood gets oxygenated. These pumping functions result from contractions of the myocardium (cardiac muscles). In a normal heart, the sinoatrial (SA) node, the heart's natural pacemaker, generates electrical pulses, called action potentials, which propagate through natural electrical conduction pathways to various regions of the heart to excite the myocardial tissue of the heart. For example, the action potentials originated from the SA node propagate through the atrioventricular (AV) node, the His bundle (also known as Bundle of His), the bundle branches, and the Purkinje fibers to activate ventricular myocardial segments, ultimately resulting in coordinated contractions in both ventricles.

Coordinated delays in the propagation of the action potentials in the natural electrical conduction system (also known as His-Purkinje system) cause the various portions of the heart to contract in synchrony to result in efficient pumping functions. A blocked or otherwise abnormal electrical conduction within the natural cardiac conduction system cause dyssynchronous contraction of the heart, resulting in poor hemodynamic performance, including a diminished blood supply to the heart and the rest of the body. In some patients, abnormal delays in the transmission of the action potentials to ventricular myocardium may reside within the His bundle. The resultant disruption of cardiac activation along the natural conduction system may cause irregular or dyssynchronous intra- and inter-ventricular contractions. This may reduce the pumping efficiency of the heart.

Artificial cardiac pacing system have been used to rectify cardiac dyssynchrony and to improve hemodynamic performance. The artificial cardiac pacing system can provide electrical stimulations to one or more portions of the heart such as to restore normal functioning of the heart to a certain extent. For example, right ventricular pacing via electrodes implanted in the apex of the RV have been used in both single ventricular and biventricular (BiV) pacing. RV apical pacing bypasses natural His-Purkinje activation and directly excites the ventricular myocardium, thus causes ventricular dyssynchrony and reduced cardiac efficiency. In some patients, the disadvantageous effects of long-term RV apical pacing are deleterious and may cause permanent changes to myocardial perfusion and structure. This remodeling process may lead to a decrease in cardiac output and deterioration of ventricular function.

BiV pacing involves RV pacing via one lead, and LV pacing via another lead, and has been demonstrated to restore substantially simultaneous contraction of both ventricles. However, BiV pacing also bypasses the His-Purkinje system. Additionally, although BiV pacing may restore ventricular synchrony and improve cardiac function to some extent in some patients, the intraventricular activations in RV or in LV is not as coordinated as with natural His-Purkinje activation. Moreover, the surgical procedure for placing the LV lead through the coronary sinus and into a vein on the left ventricular wall can be complex and challenging in some patients.

OVERVIEW

Hemodynamic response to artificial pacing can depend on many factors, including pacing site and the manner of which the pacing is performed. Many patients receiving artificial pacing therapy have an intact His bundle and the natural cardiac electrical conduction system in the ventricles, and therefore having normal ventricular activation. Conventional cardiac pacing such as long-term RV apical pacing may cause a decrease in cardiac output and efficiency due to the uncoordinated contraction sequence. This dyssynchrony may eventually cause adverse long-term effects. Dyssynchronous contraction of the ventricles occurs during conventional pacing because the propagation of the activation sequence is much slower when it occurs through working myocardium versus activation through the intrinsic specialized conduction system of the heart. The cells of the specialized conduction system propagate an activation signal about four or more times faster than working myocardium. A cardiac rhythm or functional management device configured to pace the His bundle is an alternative to conventional ventricular pacing. Pacing the His-bundle can activate the heart's natural conduction system, including the left and right bundle branches and Purkinje fibers, and thereby restore or maintain efficient and coordinated cardiac response. This may reduce or eliminate the potential long-term harmful hemodynamic effects associated with continuous RV apical pacing.

In some patients with cardiac conduction abnormalities such as bundle branch block or complete heart block, the block can be located within the His bundle. Under the theory of longitudinal dissociation, fibers within the His bundle are separated from each other by encircling layers of collagen insulation and are pre-destined for their respective bundles. His-bundle pacing (HBP) distal to the block but proximal to the bifurcation of the bundles may correct the cardiac conduction abnormalities by recruiting previously latent conduction fibers in the His bundle, restore the natural conduction, and produce global myocardial activation through the His-Purkinje system. In addition to bypassing or overcoming a structural block, the success of HBP to recruit the latent conduction fibers may also depend on overcoming a functional block in local propagation such as by applying stimulation energy to the block region. In some patients, increasing the stimulation strength of HBP may recruit fibers closely bordering the abnormal myocardium causing functional block, and mimic native conduction through the His-Purkinje system.

Although HBP has been shown to be a promising alternative to conventional RV pacing and even BiV pacing in some cases, in some patients the HBP may not effectively bypass the block and restore normal activation via the heart's natural conduction system and produce synchronous myocardial contraction. Patient response to HBP and successful correction of conduction abnormality may be related to patient His-Purkinje system anatomy, site and nature of the block in the His bundle, stimulation electrode placement, and pacing configuration, among others. There is still unmet need for a methodology to effectively identify HBP responders, i.e., those patients with correctable conduction abnormality and thus may substantially benefit from for HBP therapy.

It has also been recognized that in patients with identified correctable conduction abnormalities, the energy of pacing pulse, as well as placement and configuration of the electrodes used for HBP may vary from patient to patient. HBP, when not being used effectively, may not restore synchronous myocardial contraction. In some instances, stimulating muscle near the His bundle may cause dyssynchronous patterns similar to RV apical pacing. This undesirable effect is referred to as para-Hisian capture. In some cases, the His-bundle pacing may activate both the His bundle and the adjacent working myocardium, an event referred to as non-selective His bundle capture. However, non-selective capture may be as effective as directive pacing as the ventricular activation and contraction that results is vastly dominated by the more rapidly conducting His-Purkinje system. Therefore, there is an unmet need for an artificial cardiac pacing system that can determine the HBP stimulation strength and configuration for patients with correctable conduction abnormalities, and produce desirable therapeutic effects and patient outcome of coordinated myocardial contractions via His bundle excitation, while reducing or eliminating unintended activation of non-targeted portions of the heart, such as the para-Hisian myocardium.

Embodiments of the present subject matter provide systems, devices, and methods for pacing a cardiac conductive tissue, such as a His bundle. One example of such a medical system includes a sensing circuit to sense an intrinsic His-bundle activation of a first His-bundle portion (such as a proximal His-bundle segment), and an electrostimulation circuit to generate and deliver HBP pulses in response to the sensed intrinsic His bundle. A control circuit may time the delivery of the HBP pulse within a tissue refractory period of the first His-bundle portion subsequent to the intrinsic His-bundle activation. Based on an evoked His-bundle activation of a second His-bundle portion (such as a distal His-bundle segment) in response to the HBP pulses, the system may determine whether the intra-Hisian block has been corrected. The system may additionally include a threshold test circuit configured to determine an individualized pacing threshold representing minimal energy to excite the His bundle and to correct the cardiac conduction abnormality.

Example 1 is a system for pacing a heart having a cardiac conduction abnormality. The system comprises a sensing circuit configured to sense an intrinsic His bundle activation of a first His-bundle portion, an electrostimulation circuit configured to generate a His bundle pacing (HBP) pulse for delivery at or near the His bundle, and a control circuit coupled to the electrostimulation circuit and the sensing circuit, and configured to control the electrostimulation circuit to generate and deliver the HBP pulse according to one or more pacing parameters in response to the sensed intrinsic His bundle. The control circuit may include a timing circuit to time the delivery of the HBP pulse within a tissue refractory period of the first His-bundle portion subsequent to the intrinsic His bundle activation.

In Example 2, the subject matter of Example 1 optionally includes the sensing circuit that may be electrically coupled to one or more electrodes disposed at or near the His bundle to sense the intrinsic His bundle activation of the first His-bundle portion. The electrostimulation circuit may be electrically coupled to the one or more electrodes disposed at or near the His bundle to deliver the HBP pulse.

In Example 3, the subject matter of any one or more of Examples 1-2 optionally includes the sensing circuit that may be configured to sense the intrinsic His bundle activation within an atrio-Hisian time window beginning at a spontaneous atrial depolarization or an atrial pace event. The control circuit may be configured to control the electrostimulation circuit to generate and deliver the HBP pulse at or near the His bundle if the intrinsic His bundle activation is sensed within the atrio-Hisian time window.

In Example 4, the subject matter of Example 3 optionally includes the control circuit that may be further configured to control the electrostimulation circuit to generate and deliver a ventricular pacing pulse to a ventricle if no intrinsic His bundle activation is sensed within the atrio-Hisian time window.

In Example 5, the subject matter of any one or more of Examples 1-4 optionally includes the sensing circuit that may be further configured to sense an evoked His bundle activation of a second His-bundle portion in response to the delivery of the HBP pulse. The control circuit may be configured to generate an indicator of correction of intra-Hisian block when the evoked His bundle activation of the second His-bundle portion satisfies a specific condition.

In Example 6, the subject matter of Example 5 optionally includes the first His-bundle portion that may include right bundle fibers extending to a right bundle branch of the heart, and the second His-bundle portion that may include left bundle fibers extending to a left bundle branch of the heart. The control circuit may be configured to generate the indicator of correction of an intra-Hisian left bundle branch block when the evoked His bundle activation of the left bundle branch fibers satisfies a specific condition.

In Example 7, the subject matter of any one or more of Examples 5-6 optionally includes the sensing circuit that may be configured to sense the evoked His bundle activation including a far-field R wave in response to the delivery of HBP pulse.

In Example 8, the subject matter of Example 7 optionally includes the sensing circuit coupled to one or more electrodes disposed at or near the His bundle, or one or more electrodes disposed in an atrium, to sense the far-field R wave.

In Example 9, the subject matter of any one or more of Examples 5-6 optionally includes a physiologic sensor that may be configured to sense a hemodynamic signal. The sensing circuit may be configured to sense the evoked His bundle activation including to detect an increase in myocardial contractility from the sensed hemodynamic signal.

In Example 10, the subject matter of any one or more of Examples 5-9 optionally includes the control circuit that may include a parameter adjuster circuit configured to adjust at least one of the one or more pacing parameters if the evoked His bundle activation of the second His-bundle portion indicates no correction of intra-Hisian block. The electrostimulation circuit may be configured to generate the HBP pulse for delivery at or near the His bundle according to the adjusted at least one pacing parameter.

In Example 11, the subject matter of any one or more of Examples 1-10 optionally includes the control circuit that may include a threshold test circuit configured to determine an individualized pacing threshold representing minimal energy to excite the His bundle and to correct the cardiac conduction abnormality. The electrostimulation circuit may be configured to generate an HBP above the pacing threshold for delivery at or near the His bundle.

In Example 12, the subject matter of Example 11 optionally includes the electrostimulation circuit that may be configured to generate and deliver HBP pulse at or near the His bundle according to a pacing parameter programmed to a plurality of values. The sensing circuit may be configured to sense respective far-field R waves in response to the delivery of HBP pulse. The threshold test circuit may be configured to determine the pacing threshold based on a step change in time intervals between the delivery of HBP pulse and the sensed respective far-field R waves.

In Example 13, the subject matter of any one or more of Examples 1-12 optionally includes the control circuit that may include a pacing site selector circuit configured to determine a target His bundle pacing site for delivering the HBP pulse based on evoked His bundle activations in response to HBP pulse delivered at each of a plurality of candidate His bundle sites.

In Example 14, the subject matter of Example 13 optionally includes the evoked His bundle activations that may include far-field R waves in response to the delivery of the HBP pulse. The pacing site selector circuit may be configured to determine the target His bundle pacing site based on measurements of width of the sensed far-field R waves.

In Example 15, the subject matter of Example 13 optionally includes the evoked His bundle activations that may include hemodynamic signals in response to the delivery of the HBP pulse. The pacing site selector circuit may be configured to determine the target His bundle pacing site based on the sensed hemodynamic signals.

Example 16 is a method for pacing a heart having a cardiac conduction abnormality using a cardiac pacing system. The method comprises steps of: sensing an intrinsic His bundle activation of a first His-bundle portion using a sensing circuit; delivering a His bundle pacing (HBP) pulse generated from an electrostimulation circuit in response to the sensed intrinsic His bundle activation, the HBP pulse generated and delivered according to one or more pacing parameters; sensing an evoked His bundle activation of a second His-bundle portion using the sensing circuit in response to the delivery of the HBP pulse; and generating an indicator of correction of intra-Hisian block when the evoked His bundle activation of the second His-bundle portion satisfies a specific condition.

In Example 17, the subject matter of Example 16 optionally includes delivering the HBP pulse within a tissue refractory period of the first His-bundle portion subsequent to the intrinsic His bundle activation.

In Example 18, the subject matter of Example 17 optionally includes the first His-bundle portion that may include right bundle fibers extending to a right bundle branch of the heart, and the second His-bundle portion that may include left bundle fibers extending to a left bundle branch of the heart. The generation of the indicator of correction may include generating an indicator of correction of an intra-Hisian left bundle branch block when the evoked His bundle activation of the left bundle branch fibers satisfies a specific condition.

In Example 19, the subject matter of Example 16 optionally includes sensing the evoked His bundle activation that may include sensing a far-field R wave in response to the delivery of HBP pulse.

In Example 20, the subject matter of Example 16 optionally includes sensing the evoked His bundle activation that may include sensing a hemodynamic signal and detecting an increase in myocardial contractility from the sensed hemodynamic signal.

In Example 21, the subject matter of Example 16 optionally includes steps of adjusting at least one of the one or more pacing parameters if the evoked His bundle activation of the second His-bundle portion indicates no correction of intra-Hisian block, and generating the HBP pulse for delivery at or near the His bundle according to the adjusted at least one pacing parameter.

The systems, devices, and methods discussed in this document may improve the technology of cardiac pacing in patients with heart diseases associated with cardiac conduction abnormalities, such as bundle branch block. A technological challenge in HBP is to identify appropriate candidates with correctable conduction abnormality who would benefit from the HBP therapy. This document discusses, among other things, systems and methods for identifying HBP candidates with correctable block based on an evoked response to HBP pulses delivered within a tissue refractory period subsequent to an intrinsic His-bundle activation. The evoked HBP response provides information that may elucidate mechanism of the conduction block and predict long-term patient outcome. Another technological challenge is related to programming the HBP stimulation to achieve desirable therapeutic effects and patient outcome. This document discusses an HBP threshold test to determine appropriate individualized stimulation strength and configuration for the identified HBP candidates with correctable conduction abnormalities, such that the HBP may more efficiency utilize the natural conduction mechanisms of the heart, while reducing long-term deleterious effects on cardiac function associated with RV pacing. In addition to the improved therapeutic effect and patient outcome, the proper identification of HBP candidates and individualized pacing configuration as discussed in this document may also help reduce unnecessary medical interventions, such as drugs, procedures, or device therapies, may be scheduled, prescribed, or provided to such patients. For example, reduced unnecessary device therapy may help save battery power and extend implantable device longevity. As a result, overall system cost savings may be realized.

While His-bundle pacing is specifically discussed in this document, this is meant only by way of example and not limitation. It is within the contemplation of the inventors, and within the scope of this document, that the systems, devices, and methods discussed herein may be applied to stimulate other conductive cardiac tissue, such as the right or left bundle branches or fascicles, or the Purkinje fibers.

This Overview is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense.

The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for pacing cardiac conductive tissue. An embodiment of a His-bundle pacing (HBP) system includes an electrostimulator to generate HBP pulses for delivery at or near the His bundle. A control circuit may time the delivery of the HBP pulses within a tissue refractory period of a first His-bundle portion subsequent to an intrinsic His-bundle activation of a first His-bundle portion. Based on an evoked His-bundle activation of a second His-bundle portion such as a distal portion, the system may determine whether correction of intra-Hisian block has occurred. The system may include a threshold test circuit to determine an individualized pacing threshold representing minimal energy to excite the His bundle and to correct the cardiac conduction abnormality.

Figure 1:
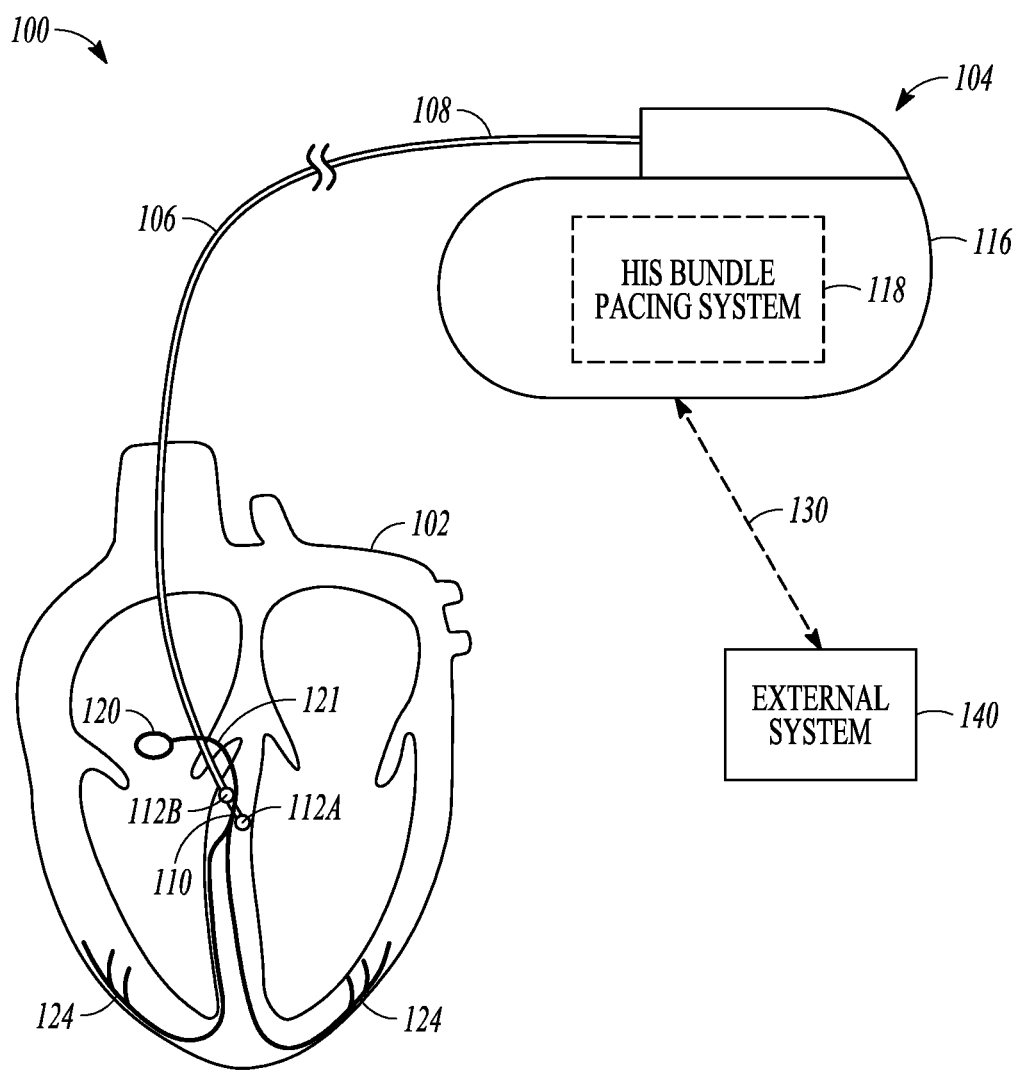
FIG. 1 illustrates generally an example of a cardiac disease management system and portions of an environment in which the system may operate.

FIG. 1 is a schematic diagram illustrating an embodiment of a cardiac disease management system 100 and portions of an environment in which the system 100 may operate. The cardiac disease management system 100 may perform a range of activities, including remote patient monitoring, diagnosis of a disease condition, and providing a therapy to treat the disease condition and to improve patient outcome. In an example, the therapy may include His-bundle pacing (HBP). One or more of these activities may be performed proximal to a patient (e.g., in the patient's home or office), through a centralized server (e.g., in a hospital, clinic or physician's office), or through a remote workstation (e.g., a secure mobile computing device).

As illustrated in FIG. 1, the cardiac disease management system 100 may be coupled to a patient's heart 102. The cardiac disease management system 100 includes an ambulatory medical device (AMD) and a lead system, configured to treat one or more cardiac diseases, such as cardiac arrhythmias or heart failure. The AMD may be an implantable device subcutaneously implanted in a chest, abdomen, or other parts of the patient, a subcutaneous monitor or diagnostic device, or a wearable medical device such as a patch-based device or a smart wearable or accessory, among others. In the example as illustrated in FIG. 1, the AMD includes an implantable medical device (IMD) 104. Examples of the IMD 104 may include a pacemaker, a pacemaker/defibrillator, a cardiac resynchronization therapy (CRT) device, a cardiac remodeling control therapy device, a neuromodulator, a drug delivery device, a biological therapy device, or an implantable diagnostic device such as a cardiac monitor or a loop recorder, among other implantable devices.

The lead system may include one or more transvenously, subcutaneously, or non-invasively placed leads or catheters. Each lead or catheter may include one or more electrodes. The arrangements and uses of the lead system and the associated electrodes may be determined by patient need and capability of the IMD 104. The associated electrodes on the lead system may be positioned at the patient's thorax or abdomen to sense a physiological signal indicative of cardiac activity, or a physiological response to stimulation of a target tissue. The lead system may be surgically inserted into, or positioned on the surface of, a heart 102. The electrodes associated with the lead system may be disposed in a target site in a right atrium (RA), a right ventricle (RV), a left atrium (LA), or a left ventricle (LV), or other body parts. Stimulation energy may be delivered to a target site via one or more of these electrodes. Some electrodes may be used for sensing cardiac activity, such as an intrinsic or evoked cardiac electrical activity.

In the illustrated example, the lead system may include a lead 106 having a proximal end 108 configured to be connected to the IMD 104, and a distal end 110 that includes one or more electrodes configured to deliver stimulation energy, such as in a form of pacing pulses, to the His bundle 121. FIG. 1 illustrates, by way of example and not limitation, two electrodes including a tip electrode 112A and a ring electrode 112B. Additional electrodes may be included in the lead 106 for sensing electrical activity or for delivering stimulation energy. The lead 106 may be placed such that one or more electrodes, such as 112A-B, are positioned in or on a His bundle 121, a region distal to the blocked or slowly conducting AV node and in the AV septum, an interventricular septum region, or a right atrial region near the His-bundle 121. As part of the natural electrical conduction system of the heart 102, the His bundle 121 transmits the electrical impulses from the AV node 120 to the point of the apex of the fascicular branches via the left bundle branch 122 and the right bundle branch 123. Each of the left and right branch bundles leads to the Purkinje fibers 124, which provide electrical conduction to the ventricles, causing the ventricles to contract. In some examples, the lead 106 may be placed such that one or more electrodes associated with the lead 106, such as 112A-B, are positioned at or near other parts of the natural conduction pathways, such as one of the bundle branches 122 or 123, the Purkinje fibers 124, or other conductive tissues, in addition to or in lieu of a region at or near the His bundle 121.

In an example, the lead 106 may be a single pass lead having a plurality electrodes for stimulating multiple cardiac sites, including electrodes disposed at or near the His bundle (e.g., the electrodes 112A-B) and electrodes disposed in one or more of RA, RV, LA, or LV of the heart 102. In some examples, in addition to the lead 106, the lead system may include separate leads for placement in different heart chambers or sites, such as an RA lead having one or more RA electrodes to stimulate a portion of RA or to sense RA electrical activity, a RV lead having one or more RV electrodes to stimulate a portion of RV or to sense RV electrical activity, or an LV lead having one or more LV electrodes to stimulate a portion of LV or to sense LV activity. In various examples, the cardiac disease management system 100 may include one or more leadless stimulators/sensors untethered to a lead and in wireless communication with the IMD 104. The leadless stimulators/sensors may deliver electrostimulation, sense a physiological signal, such as cardiac electrical signals in response to cardiac stimulation, and transmit the sensed data to the IMD 104.

The IMD 104 may include a hermetically sealed housing 116 that houses one or more of an electrostimulation circuit, a sensing circuit, a control circuit, a communication circuit, and a battery, among other components. In an example, the IMD 104 includes a His-bundle pacing system 118 configured to generate His-bundle pacing (HBP) pulses for delivery at or near the His bundle 121, such as via the lead 106 and the associated electrodes 112A or 112B. The His-bundle pacing system 118 may be programmed to deliver unipolar His-bundle pacing, where the pacing energy (current or voltage) is applied between one of the electrodes 112A-B (e.g., as a cathode) and the housing 116 (e.g., as an anode). Alternatively, the His-bundle pacing system 118 may be programmed to deliver bipolar His-bundle pacing, where the pacing energy (current or voltage) is applied between two electrodes positioned at or near the His bundle, such as between the electrodes 112A and 112B. In some examples, electrodes used for unipolar or bipolar His-bundle pacing may be selected by a system user from a plurality of candidate electrodes from one or more leads of the lead system, and programmed into the His-bundle pacing system 118.

The His-bundle pacing system 118 may sense a physiological signal using one or more electrodes associated with the lead system or a physiological sensor. Examples of the physiological signal may include an electrocardiogram (ECG), an intracardiac electrogram (EGM) such as an atrial EGM, a ventricular EGM, or a His bundle EGM, an thoracic impedance signal, a cardiac impedance signal, an arterial pressure signal, a pulmonary artery pressure signal, a left atrial pressure signal, an RV pressure signal, an LV coronary pressure signal, a coronary blood temperature signal, a blood oxygen saturation signal, a heart sound signal, an intracardiac acceleration signal, a respiration signal, or a physical activity or exertion level signal, among others.

The His-bundle pacing system 118 may detect an intrinsic His-bundle activation using one or more electrodes such as electrodes 112A or 112B. Additionally, the His-bundle pacing system 118 may sense a cardiac electrical or mechanical signal representing an evoked response to the delivery of HBP pulses. The His-bundle pacing system 118 may deliver HBP pulses subsequent to the detection of the intrinsic His-bundle activation. In an example, the HBP pulse may be delivered within a tissue refractory period of the first His-bundle portion. The cardiac electrical or mechanical signal may be sensed using one or more electrodes or physiologic sensors. In an example, the His-bundle pacing system 118 may sense a far-field cardiac electrical signal representative of ventricular contractions using electrodes disposed at or near the His bundle (e.g., one or more of the electrodes 112A and 112B), or electrodes disposed in an atrium. The His-bundle pacing system 118 may verify His bundle capture using the sensed far-field cardiac electrical signal. In an example, the His-bundle pacing system 118 may detect a His-bundle capture directly resulting from the delivery of HBP pulses, or a myocardial capture directly resulting from the delivery of HBP pulses. In another example, the His-bundle pacing system 118 may classify a tissue response into one of a plurality of capture types.

The His-bundle pacing system 118 may determine if the evoked His-bundle activation of at least a second His-bundle portion indicates correction of intra-Hisian block, based on the far-field cardiac electrical signal. An example of second His-bundle portion includes a distal His-bundle portion. If the evoked His-bundle activation of the second His-bundle portion indicates no correction of intra-Hisian block, then His-bundle pacing system 118 may adjust at least one of the pacing parameters. In some examples, the His-bundle pacing system 118 may determine a target His-bundle pacing site for delivering the HBP pulse based on the evoked His-bundle activations at each of a plurality of candidate His bundle sites.

The IMD 104 may be configured to communicate with an external system 140 via a communication link 130. The external system 140 may include a dedicated hardware/software system such as a programmer, a remote server-based patient management system, or alternatively a system defined predominantly by software running on a standard personal computer. The external system 140 may include a proximal external device such as a programmer device in proximity of the IMD 104. A clinician may manage the patient 102 through the IMD 104 via the communication link 130. This may include, for example, programming the IMD 104 to sense physiological signals, analyzing the physiological signals to detect a medical condition such as heart failure, assessing therapy efficacy, performing a self-diagnostic test, or initiating or adjusting a therapy such as HBP. Additionally, the external system 140 may receive device data from the IMD 104 via the communication link 130. Examples of the device data may include real-time or stored physiological signals collected from the patient 102, physiological response to therapies delivered to the patient 102, or device operational status of the IMD 104 (e.g., battery status and lead impedance). The communication link 130 may be an inductive telemetry link, a capacitive telemetry link, or a radio-frequency (RF) telemetry link, or wireless telemetry based on, for example, "strong" Bluetooth or IEEE 802.11 wireless fidelity "WiFi" interfacing standards. Other configurations and combinations of patient data source interfacing are possible.

The external system 140 may monitor patient condition and the function of IMD 104. In various embodiments, the external system 140 may include a user interface to display received information to the user, and receive user input for operation control of the IMD 104. In an example, the external system 140 may be configured to verify pacing capture status, or classify tissue response to one of a plurality of capture types. The capture verification or classification may be carried out periodically, or triggered by a specific event such as a user command. A user may use the external system 140 to program the IMD 104, such as to configure a pacing vector (e.g., specifying anode and cathode electrodes) to deliver HBP, or to configure a sense vector to sense a physiological signal.

The external system 140 may include a remote device in a location relatively distant from the IMD 104 and in communication with the proximal external device via a telecommunication network. The remote device can evaluate collected patient data and provide alert notifications, among other possible functions. In an example, the remote device may include a centralized server acting as a central hub for collected patient data storage and analysis. The server may be configured as a uni-, multi- or distributed computing and processing system. The server may include an alert analyzer circuit to evaluate the collected patient data to determine if specific alert condition is satisfied. Satisfaction of the alert condition may trigger a generation of alert notifications. In some examples, the alert conditions alternatively or additionally may be evaluated by the IMD 104. By way of example, alert notifications may include a Web page update, phone or pager call, E-mail, SMS, text or "Instant" message, as well as a message to the patient and a simultaneous direct notification to emergency services and to the clinician. Other alert notifications are possible. In various examples, the remote device may additionally include one or more locally configured clients or remote clients securely connected over the telecommunication network to the server. Examples of the clients may include personal desktops, notebook computers, mobile devices, or other computing devices. System users, such as clinicians or other qualified medical specialists, may use the clients to securely access stored patient data assembled in the database in the server, and to select and prioritize patients and alerts for health care provisioning.

The external system 140 may output the detected medical events or therapy efficacy information (such as capture verification or classification) to a system user such as the patient or a clinician, or to a process including, for example, an instance of a computer program executable in a microprocessor. In an example, the process may include an automated generation of recommendations for initiating or titrating a medical therapy or an electrostimulation therapy. In an example, the external device 120 or the remote device 124 may include a respective display unit for displaying the physiological signals, stimulation parameters, capture verification, or classification of capture types, among other intermediate analyses and computations. Alerts, alarms, emergency calls, or other forms of warnings to signal the detected medical event may also be generated.

Portions of the IMD 104 or the external system 140 may be implemented using hardware, software, firmware, or combinations thereof. Portions of the IMD 104 or the external system 140 may be implemented using an application-specific circuit that may be constructed or configured to perform one or more functions, or may be implemented using a general-purpose circuit that may be programmed or otherwise configured to perform one or more functions. Such a general-purpose circuit may include a microprocessor or a portion thereof, a microcontroller or a portion thereof, or a programmable logic circuit, a memory circuit, a network interface, and various components for interconnecting these components. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
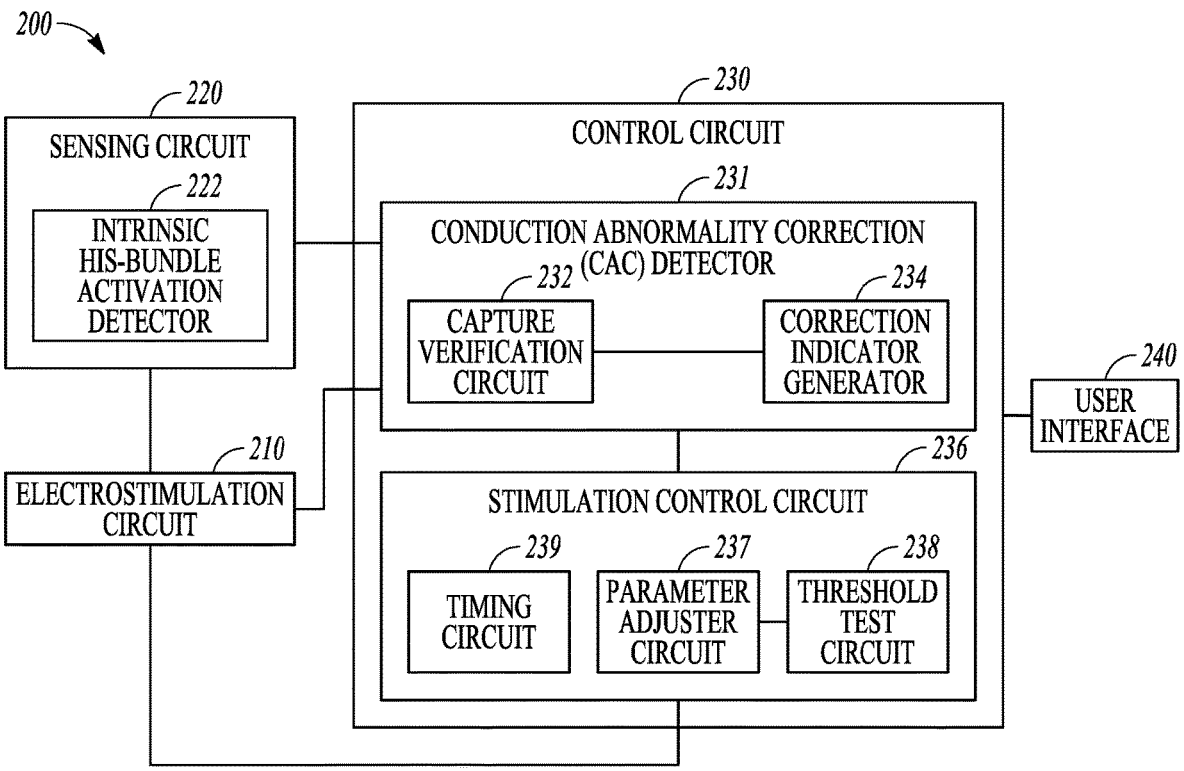
FIG. 2 is a block diagram illustrating an embodiment of portions of a His-bundle pacing system.

FIG. 2 is a block diagram illustrating an embodiment of portions of a His-bundle pacing system 200. The His-bundle pacing system 200 represents an embodiment of the His-bundle pacing system 118, and may include an electrostimulation circuit 210, a sensing circuit 220, a control circuit 230, and a user interface 240.

The electrostimulation circuit 210 may be configured to generate stimulation energy for delivery to the heart 102 via one or more leads and the associated electrodes. The electrostimulation circuit 210 may be configured to generate His-bundle pacing (HBP) pulses for delivery to a target site at or near the His bundle such as via the lead 106 and one or more of the electrodes 112A-B. The target site may include an interventricular septum region or a right atrial region near the His-bundle, or other conductive tissues such as right or left bundle branches or fascicles, or Purkinje fibers. In an example, the HBP pulses may be delivered in multiple cardiac cycles. In various examples, the electrostimulation circuit 210 may additionally generate electrostimulation for delivery at non-cardiac tissues such as nerve tissues, muscle tissues, or other excitable tissues.

The electrostimulation circuit 210 may generate the HBP pulses according to programmed stimulation parameters, such as provided by the control circuit 230. Examples of the stimulation parameters may include information about stimulation site, stimulation strength, stimulation mode, or stimulation timing, among other parameters. Stimulation site includes information about pacing site, pacing vector configuration (e.g., anode and cathode electrodes), or unipolar or bipolar pacing. The stimulation site may additionally include cardiac resynchronization therapy (CRT), which include (BiV) pacing of both left and right ventricles, or synchronized left ventricle (LV)-only pacing; single site pacing of only one site of a heart chamber (e.g., the left ventricle) within a cardiac cycle; or multisite pacing (MSP) of two or more sites of a heart chamber within the same cardiac cycle. Stimulation strength parameters determine the amount of energy delivered to the pacing site, and may include pulse amplitude, pulse width, pulse frequency, pulse waveform, duty cycle, or stimulation duration.

Stimulation mode may include a singular Hisian (H-only) pacing mode, an atrial-Hisian (AH) pacing mode, a His-ventricular (HV) pacing mode, or an atrial-His-ventricular (AHV) pacing mode. AH pacing mode may be used to treat patients with varying degrees of heart block or sick sinus syndrome. In the AH pacing mode, the HBP pulses may be delivered when intrinsic atrial activation (As), or atrial pacing (Ap), fails to produce propagatable depolarization of the AV node and the His bundle. HV or H-only pacing mode may be indicated for patients with persistent or chronic atrial fibrillation, who require atrioventricular node ablation to slow and regularize ventricular rhythm. The HV pacing mode involves sequential pacing of the His bundle with ventricular pacing in the event of non-conduction. The ventricular pacing may be provided in a demand mode, such that the ventricular pacing pulses are delivered only when the His pacing fails to produce propagatable depolarization of the ventricles. Delivery of the ventricular pacing pulses or a detection of PVC may trigger a ventriculoatrial interval for sensing an intrinsic atrial activation or for timing the delivery of atrial pacing in the next cardiac cycle. The AHV pacing mode involves sequential atrial, Hisian, and ventricular pacing. One or more of the His-bundle pacing or the ventricular pacing may be delivered in a demand mode. AHV pacing mode may be indicated for patients with cardiac dysynchrony and having received cardiac resynchronization therapy, patients suffering from heart failure with left bundle branch block, heart failure induced by right ventricular pacing, long PR intervals with hemodynamic compromise, or pacemaker induced cardiomyopathy from conventional dual-chamber pacing.

Stimulation timing parameters determine the timing and sequence of pacing pulses. For example, in demand AH pacing mode, the HBP pulses are timed relative to an As or an Ap event. An AH timing represents a latency period, within a cardiac cycle, from an intrinsic As event or an Ap event to the delivery of an HBP pulse. In demand HV pacing mode, the ventricular pacing pulses are timed relative to a His pacing event. An HV timing represents a latency period, within a cardiac cycle, from a His bundle event (e.g., an HBP pulse) to the delivery of ventricular pacing pulse. In an example, if an HBP pulse fails to induce ventricular depolarization, a backup ventricular pacing may be delivered at the end of the HV timing. The stimulation timing parameters may additionally include parameters associated with CRT or MSP therapy, such as atrial-ventricular delay (AVD) representing a latency period from an As or Ap event to ventricular pacing, an RV-LV interventricular pacing delay (VVD) representing a time delay between ventricular pacing at the left and right ventricles, or intra-ventricular pacing delay representing a time delay between pacing at multiple site of a ventricle.

The electrostimulation circuit 210 may be configured to provide selective pacing at a site with only a targeted tissue being directly excited, without substantial unintended and undesirable excitation of other non-targeted tissue. If the pacing directly causes intended excitation of the targeted tissue as well as unintended excitation of other non-targeted tissue, a non-selective pacing results. In the context of HBP as discussed in this document, the "selective His-bundle pacing" refers to delivering HBP pulses, at or near a His bundle region, which causes only the excitation (depolarization) of the His bundle, without substantial unintended and undesirable excitation of the muscle tissue adjacent to the His bundle (also known as the para-Hisian myocardium) directly caused by the pacing pulses. The "non-selective His-bundle pacing" refers to delivering HBP pulses that causes the both the excitation (depolarization) of the His bundle, and unintended excitation of para-Hisian myocardium directly caused by the pacing pulses. In some examples, the HBP is a "para-Hisian pacing", when the delivery of the HBP pulses causes only excitation of the para-Hisian myocardium or other un-intended cardiac tissues, without substantial intended excitation of the His bundle directly caused by the pacing pulses.

The sensing circuit 220 may be coupled to one or more electrodes or physiologic sensors to sense electrical or mechanical activity of a portion of the heart 102. The sensing circuit 220 may include an intrinsic His-bundle activation detector 222 configured to sense an intrinsic His-bundle activation using one or more electrodes such as electrodes 112A or 112B. The intrinsic His-bundle activation may be an electrical signal representative of depolarization of a first His-bundle portion (such as a proximal His-bundle segment), rather than the entire His bundle region. The intrinsic His-bundle activation may result from a spontaneous sinus node firing which is hereinafter referred to as an atrial sense (AS) event, or in response to pacing at an atrium which is hereinafter referred to as an atrial pace (Ap) event. In an example, the sensing circuit 220 is configured to sense the intrinsic His-bundle activation within an atrio-Hisian (AH) time window beginning at an As event or an Ap event in a cardiac cycle, and sustains for a specified duration. An intrinsic His-bundle activation (Hs) sensed during the AH window may trigger the delivery of an HBP pulse at or near the His bundle, such as controlled by the stimulation control circuit 236. Examples of the timing sequence of intrinsic His-bundle activation and the triggered HBP are discussed below, such as with reference to FIGS. 4A-C.

The sensing circuit 220 may additionally sense a cardiac electrical or mechanical signal representing an evoked response to the delivery of HBP pulses. The HBP pulses may be delivered at a time subsequent to the detection of the intrinsic His-bundle activation. In an example, the HBP pulse may be delivered within a tissue refractory period of the first His-bundle portion. Examples of the sensed signals may include: an electrocardiogram (ECG); an electrogram (EGM) of a portion of the heart such as atrial EGM, ventricular EGM, or evoked His potential; an impedance signal; a heart sound signal; or a pressure signal, among other physiological or hemodynamic signals indicative of a tissue response to the delivery of HBP pulses.

In some examples, the sensing circuit 220 may be coupled to a physiologic sensor to detect an increase in myocardial contractility from the sensed hemodynamic signal, representing a hemodynamic response to the delivery of the HBP pulses. In some examples, the sensing circuit 220 may be configured to sense a far-field cardiac electrical signal representing ventricular response to the delivery of the HBP pulses. In an example, the far-field cardiac electrical signal may be sensed using a unipolar sense vector comprising an electrode disposed at or near the His bundle or in an atrium, and a reference electrode distal to the His bundle, such as the housing 116 of the IMD 104. In another example, the far-field cardiac electrical signal may be sensed using a bipolar sense vector comprising two electrodes disposed at or near the His bundle or in an atrium. The electrode(s) for sensing the far-field cardiac electrical signal may be the same electrodes used for delivering HBP pulses. Alternatively, different electrodes may be used for sensing the far-field cardiac electrical signal. Compared to the near-field signal sensed directly from an electrode disposed in the ventricle, the far-field cardiac electrical signal does not require electrodes in direct contact with the ventricle. As such, it may be particularly suitable for patients without an implantation of a dedicated ventricular lead. Far-field signals may also provide a global perspective to the activation of the heart. For example, both atrial and ventricular activity may be present on a far-filed signal. Furthermore, the far-field signal characteristics such as the morphology may provide information about the type of activation, for example normal ventricular activation vs. a PVC. The sensed far-field cardiac electrical signal may be used by the control circuit 230 to verify His bundle capture.

In some examples, portions of the His-bundle pacing system 200 may be implemented distributedly between two devices. In an example, a first device may include the electrostimulation circuit 210 and a stimulation delivery system such as the lead and associated electrodes for delivering the HBP pulses, and a second device may include the sensing circuit 220 and at least a portion of the control circuit 230. The sensing circuit 220 of the second device may be configured to sense, among other signals, intrinsic His bundle activities and the far-field ventricular response to the HBP pulses. In an example, the first and second devices are both implantable devices. In another example, at least one of the first or the second device is a non-implantable, wearable device.

The control circuit 230 may be configured to control the electrostimulation circuit to generate and deliver the HBP pulse in response to the sensed intrinsic His bundle, verify that the HBP pulses capture one or more of the conductive tissues (such as the His bundle or the myocardium), and determine whether the HBP pulses have corrected the conduction abnormality in the His bundle. In an example, the control circuit 230 can be implemented as a part of a microprocessor circuit in the cardiac disease management system 100. The microprocessor circuit can be a dedicated processor such as a digital signal processor, application specific integrated circuit (ASIC), microprocessor, or other type of processor for processing information including heart sounds. Alternatively, the microprocessor circuit can be a general-purpose processor that can receive and execute instructions of performing the functions, methods, or techniques described herein.

As illustrated in FIG. 2, the control circuit 230 may include circuit sets comprising a conduction abnormality correction (CAC) detector 231 and a stimulation control circuit 236. The CAC detector 231 may further include a capture verification circuit 232 and a correction indicator generator 234. These circuits, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The capture verification circuit 232 may be coupled to the electrostimulation circuit 210 and the sensing circuit 220, and configured to verify His bundle capture using the sensed far-field cardiac electrical signal. The capture verification circuit 232 may perform capture verification according to a specified schedule, such as on a periodic basis, or continuously on a beat-by-beat basis (i.e., verifying capture in response to each HBP pulse). In an example, the capture verification circuit 232 may detect His bundle capture directly resulting from the delivery of the HBP pulse, and myocardial capture directly resulting from the delivery of the HBP pulse. The electrostimulation circuit 210 may deliver the HBP pulses at specified time, as controlled by the stimulation control circuit 236. In an example, the HBP pulses may be delivered during a refractory period of the first portion of the His-bundle tissue that have intrinsically depolarized. The HBP pulses may be delivered in multiple cardiac cycles, such that at least one pulse is delivered in each of the multiple cardiac cycles. In various examples, the detection of the His-bundle capture and the myocardial capture may be based on timing of a far-field ventricular event in response to the delivery of HBP pulses, or a morphology of the far-field ventricular activity, as to be discussed in the following with reference to FIG. 3.

The correction indicator generator 234, coupled to the capture verification circuit 232, may generate an indicator of correction of intra-Hisian block when the evoked His-bundle activation of the second His-bundle portion satisfies a specific condition. In an example, a correction of intra-Hisian block is deemed to have occurred if the capture verification circuit 232 detects a His-bundle capture without myocardial capture (i.e., a selective His-bundle capture), or a His-bundle capture along with myocardial capture (i.e., a non-selective His-bundle capture). No correction of intra-Hisian block is deemed to have occurred if no His-bundle capture is detected within a specified evoked-response detection window. The first His-bundle portion may be a proximal His-bundle segment, and the second His-bundle portion may be a distal His-bundle segment. In an example, the first His-bundle portion includes right bundle fibers extending to a right bundle branch of the heart, and the second His-bundle portion includes left bundle fibers extending to a left bundle branch of the heart. In response to an intrinsic His-bundle activation at the first His-bundle portion, HBP pulses may be delivered within the refractory period of the first His bundle. If the capture verification circuit 232 detects from the evoked response a His bundle capture of at least the second His-bundle portion with or without myocardial capture, then the correction indicator generator 234 may generate an indication that a correction of an intra-Hisian left bundle branch block has occurred.

The stimulation control circuit 236 controls the generation and delivery of electrostimulation such as HBP pulses. The stimulation control circuit 236 may include one or more of a parameter adjuster circuit 237, a threshold test circuit 238, and a timing circuit 239. The parameter adjuster circuit 237 may adjust at least one of the stimulation parameters if the evoked His-bundle activation of the second His-bundle portion indicates no correction of intra-Hisian block, such that no correction indicator is generated from the correction indicator generator 234. By adjusting at least one stimulation parameter, the HBP may more likely correct the intra-Hisian block, activate patient natural conduction system more effectively, and therefore improve cardiac performance.

The parameter adjustment may be attempted periodically at specified period, or triggered by a specific event. The parameter adjustment may be automatically executed, or programmed by a user (e.g., a clinician) via a user interface 240. Various stimulation parameters may be adjusted. In an example, the parameter adjuster circuit 237 may adjust stimulation site, such as by switching to a different stimulation vector configuration including an electrode in close proximity to the His bundle to improve the likelihood of selectively capturing the His-bundle. In another example, the parameter adjuster circuit 237 may adjust stimulation timing, such as the AH timing relative to an intrinsic or paced atrial event. In an example, the parameter adjuster circuit 237 may adjust stimulation strength, such as one or more of pulse amplitude, pulse width, pulse frequency, pulse waveform, duty cycle, or stimulation duration. In an example, the parameter adjuster circuit 237 may adjust stimulation mode, such as switching from AH mode to HV mode when a patient develops persistent or chronic atrial fibrillation, or treated with atrioventricular node ablation. In another example, the parameter adjuster circuit 237 may switch from AH pacing mode to AHV mode in response to a change in patient condition, such as a development of bundle branch block. AHV mode may also be used in patients with an AH indication, such as to provide backup ventricular pacing via a ventricular lead in case that HBP pulses do not always induce ventricular depolarization. Additionally, the AHV mode may be used in CRT patients who already have an RV lead implanted for cardiac pacing and optionally defibrillation therapy. In an example, the parameter adjustment may be continued until the His-bundle capture is detected.

Improper assessment of HB threshold can result in para-Hisian capture and ventricular dyssynchrony. Para-Hisian capture refers to excitation of only the para-Hisian muscle without excitation of the His bundle directly caused by the delivery of HBP pulses. The pacing threshold test circuit 238 may be configured to determine a pacing threshold representing minimal energy required to excite the His bundle. In various examples, the parameter adjuster circuit 237 may adjust one or more stimulation parameters using the determined pacing threshold. The pacing threshold may be determined during implant of the IMD 104, periodically at specified time period, or triggered by a specific event, such as the HBP pulses failing to excite the His bundle, or a user command. The threshold test may include delivering HBP pulses (e.g., via the electrostimulation circuit 210) at or near the His bundle in accordance with a threshold test protocol. The threshold test protocol defines varying a stimulation parameter at a specified manner, such as ramping up or ramping down the pulse amplitude. The capture verification circuit 232 may measure time intervals (HV interval) between the delivery of HBP pulses with varying pulse amplitude and the corresponding sensed far-field ventricular responses, such as far-field R (FFR) wave or far-field QRS complexes (FF-QRS). The FF-QRS or FFR waves may be detected in a capture detection window ($W_D$) that begins at the delivery of HBP pulse and has a window duration of L. To ensure proper detection of FF-QRS or FFR waves, the window duration L may be initialized to approximately 150 msec. A central tendency measure of the HV intervals ($HV_C$), such as an average or a median of the HV intervals over a plurality of cardiac cycles (e.g., 5-10 cardiac cycles), may be determined. The window duration L may then be updated to be greater than the $HV_C$ by a specified margin $\delta$, that is, $L=HV_C+\delta$. Alternatively, the detection window ($W_D$) may be defined as a neighborhood of the $HV_C$. In an example, $W_D$ begins at $HV_C-15$ msec, and ends at $HV_C+15$ msec.

The threshold test circuit 238 may be configured to determine an individualized pacing threshold representing minimal energy to excite the His bundle and to correct the cardiac conduction abnormality. The threshold test circuit 238 may be coupled to the capture verification circuit 232 to detect a step change in the measured HV interval in response to the delivery of the HBP pulses with varying pulse amplitude. For example, a step increase in HV interval indicates a transition from a propagatable His-bundle excitation to a para-Hisian myocardium only excitation without His-bundle capture. The threshold test circuit 238 may determine the pacing threshold to be the pulse amplitude corresponding to the detected step change in the measured HV interval. In an example, the pulse amplitude is decremented on every 3-5 beats, until the threshold test circuit 238 detects a step increase in the measured HV interval by at least 30 msec. The threshold test circuit 238 may determine the pacing threshold to be the highest pulse amplitude that results in the detected step increase in the measured HV interval. The parameter adjuster circuit 237 may adjust the stimulation strength, such as the His-bundle pacing amplitude, based on the pacing threshold. In an example, the His-bundle pacing amplitude may be adjusted to be 3-5 times the pacing threshold for an improved performance of His-bundle capture.

In some examples, the pacing threshold test circuit 238 may determine the pacing threshold using the morphology of the far-field ventricular response, such as FF-QRS or FFR wave. The threshold test circuit 238 may monitor the FF-QRS or FFR wave and detect a change in wave morphology in response to the delivery of the HBP pulses with varying pulse amplitude. The change in wave morphology, such as a change in FF-QRS or FFR wave width, indicates a transition from a propagatable His-bundle excitation to a para-Hisian myocardium only excitation without His-bundle capture. The threshold test circuit 238 may determine the pacing threshold to be the pulse amplitude corresponding to the detected change in FF-QRS or FFR wave morphology.

In various examples, the capture verification circuit 232 may additionally or alternatively use mechanical or hemodynamic sensors to determine the capture status, including detecting the His bundle response and myocardial response, or classifying a tissue response into one of capture types. Zhu et al. U.S. Pat. No. 8,688,234, entitled "DEVICES, METHODS, AND SYSTEMS INCLUDING CARDIAC PACING," refers to determining the effectiveness or completeness of His-bundle capture using attributes of a QRS signal, such as QRS narrowing, or using mechanical or hemodynamic sensors, which is incorporated herein by reference in its entirety. Dong et al. U.S. Pat. No. 8,565,880 entitled "HIS-BUNDLE CAPTURE VERIFICATION AND MONITORING," refers to His-bundle capture verification using hemodynamic sensors such as heart sound or blood pressure sensors, which is incorporated by reference herein in its entirety.

The timing circuit 239 may be configured to time the delivery of the HBP pulses according to a stimulation timing parameter, such as an adjusted stimulation timing provided by the parameter adjuster circuit 237 or programmed by a user via a user interface 240. In an example, the timing circuit 239 may time the delivery of an HBP pulse using an atrio-Hisian (AH) window. The AH window is a programmable latency period with respect to an intrinsic (As) or paced atrial event (Ap). In an example, the AH window may be programmed to approximately 50 msec shorter than a sensed P wave-to-R wave (PR) interval or a programmed atrial-to-ventricular (AV) delay within a cardiac cycle. If an intrinsic His-bundle activity (Hs) is sensed within the AH window, the timing circuit 239 may initiate a His refractory period, during which an HBP pulse may be delivered. In another example, the AH window may be determined based on an intrinsic AH interval, such that the AH window may be programmed to slightly longer than the intrinsic AH interval (e.g., approximately 1-30 milliseconds longer than the intrinsic AH interval). The HBP would then be timed off a sensed atrial event but would occur just after the anticipated His event. The delivery of the HBP pulse may trigger a His capture verification window during which an evoked response, such as a FF-QRS or FFR wave or a hemodynamic signal may be sensed.

In an example, a system user may program an AV delay and an HV interval, such that that AH timing may be determined as AH=AV−HV. The HV interval may be programmed to approximately 50-80 msec, which determines how far in advance to the end of the AV delay that the HBP pulse is delivered. The AV delay may be a sensed AV delay between an As event and a ventricular pacing pulse in the same cardiac cycle, or a paced AV delay between an Ap event and a ventricular pacing pulse in the same cardiac cycle. The paced AV delay may be programmed to be a slightly longer to allow for atrial pace latency and intra-atrial conduction delay. Examples of the timing sequence and various detection windows are discussed below, such as with reference to FIG. 4.

In various examples, the electrostimulation circuit 210 may be configured to generate backup pacing pulses for delivery to the heart to excite the myocardium and prevent asystole. The backup pacing pulses may be delivered only if a loss of capture is indicated, characterized by neither the para-Hisian myocardium capture nor the His bundle capture by the delivery of HBP pulses within the capture detection window $W_D$. In another example, the backup pacing pulses may be delivered when the HBP pulses cause para-Hisian myocardium only excitation, without the His bundle excitation. The backup pacing may be delivered to a target ventricular site via a lead with associated electrodes disposed in or on a ventricle, such as a right ventricle. Additionally or alternatively, the backup pacing may be delivered to the His bundle, such as the site for delivering HBP pulses, via the same His-bundle pacing lead with associated electrodes.

The timing circuit 239 may time the delivery of the backup pacing at the end of the capture detection window $W_D$. Alternatively, the timing circuit 239 may time the delivery of a backup pacing at the end of a programmable atrio-ventricular (AV) delay that begins at an As or an Ap event. Upon the expiration of the AV delay, or reaching the end of the capture detection window $W_D$, the timing circuit 239 may initiate a VA timer to detect an As event, or to initiate delivery of an Ap pulse upon the expiration of the VA timer, which marks the beginning of a new cardiac cycle. If the HBP pulse results in His bundle capture or para-Hisian myocardium capture, the timing circuit 239 may initiate the VA timer upon the detection of the far-field ventricular activity (such as the FF-QRS or FFR wave) within the capture detection window $W_D$. In an example, an ectopic ventricular beat, such as a PVC, may be sensed in the His bundle region or in the atrium, and trigger the VA timer. Compared to conventional pacing system which triggers the VA timer off the delivery of ventricular pacing (such as RV apical pacing), the VA timer triggered by the sensed FF-QRS or FFR wave (in the case of His bundle capture and conducted R-wave) or by the expiration of the capture detection window $W_D$ (in the case of no FF-QRS or FFR wave detection) is more suitable for AH pacing mode in which the ventricular pacing is infrequently delivered and may be only reserved as a backup therapy.

The user interface 240 may include an input unit and an output unit. In an example, at least a portion of the user interface 240 may be implemented in the external system 140. The input unit may receive user input such as values of the parameters for physiologic event sensing, and His bundle response and myocardial response detections. The user input may receive user programming of stimulation parameters, or confirmation, rejection, or otherwise modification of the stimulation parameters generated by the parameter adjuster circuit 237. The input unit may include an input device such as a keyboard, on-screen keyboard, mouse, trackball, touchpad, touch-screen, or other pointing or navigating devices. The output unit may include circuitry configured to generate a human-perceptible notification of His bundle response and myocardial response and capture status. The output circuit may be coupled to a display for displaying the received physiologic signals, including tracings of one or more of atrial electrogram, His bundle electrogram, ventricular electrogram, surface electrocardiogram, or other sensor signals. The display may also display event sensing information such as intrinsic depolarizations, paced events (such as HBP pulses), and timing information on each of the sensed signals. The event sensing information may be overlaid with the signal tracings, or be displayed in a separate marker channel. The stimulation parameters, and intermediate measurements or computations may also be displayed. The output circuit 230 may be coupled to a printer for printing hard copies of information about the event detection and therapy titration protocol. The information may be presented in a table, a chart, a diagram, or any other types of textual, tabular, or graphical presentation formats. The presentation of the output information may include audio or other media formats. In an example, the output unit may generate alerts, alarms, emergency calls, or other forms of warnings to signal the system user about the His bundle capture status. In an example, the output unit may generate an alert when a loss of capture is indicated and a backup pacing is delivered. In another example, frequent backup pacing delivery may trigger the output unit to generate an alert and prompt a user (e.g., a clinician) to reprogram the pacing system.

Figure 3:
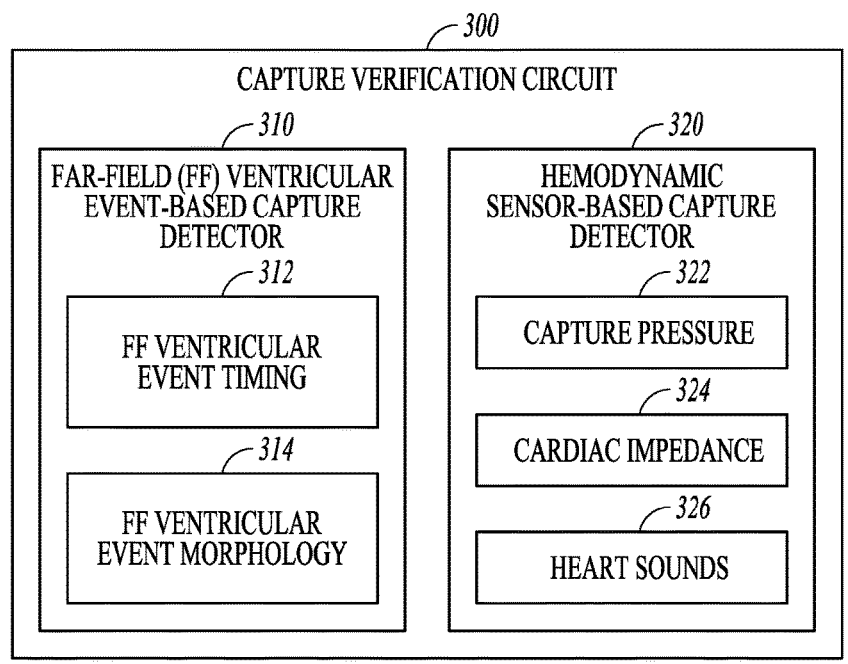
FIG. 3 illustrates generally an example of a capture verification circuit.

FIG. 3 illustrates generally an example of a capture verification circuit 300, which is an embodiment of the capture verification circuit 232. The capture verification circuit 300 may include one or more of a far-field (FF) ventricular event-based capture detector 310, or a hemodynamic sensor-based capture detector 320. Based on the capture status as determined based on the FF ventricular event-based capture detector 310 or the hemodynamic sensor-based capture detector 320, the correction indicator generator 234 may generate an indicator of correction of intra-Hisian block.

The FF ventricular event-based capture detector 310 may detect capture status based on FF ventricular event timing 312 or FF ventricular event morphology 314, both of which may be determined using a cardiac electrical signal, such as sensed by the sensing circuit 220. Examples of the FF ventricular event may include FF-QRS or FFR wave sensed at or near the His bundle or in an atrium.

In an example, a bipolar far-field cardiac electrical signal may be sensed using two electrodes disposed at or near the His bundle or in an atrium. Such a bi-polar far-field cardiac electrical signal may provide accurate FF ventricular event timing 312. In an example, the capture verification circuit 232 may measure a time interval (HV interval) between an HBP pulse and an evoked far-field ventricular activity, such as a FF-QRS or FF-R wave. Generally, a His-bundle response may be characterized by a short HV interval due to faster propagation of the His bundle depolarization through the His-Purkinje system (including His bundle, bundle branches, and Purkinje fibers). In contrast, a myocardial response may be characterized by a relatively longer HV interval due to relatively slower, cell-to-cell conduction of the depolarization.

In an example, a unipolar far-field cardiac electrical signal may be sensed between an electrode disposed at or near the His bundle or in an atrium, and a reference electrode such as the housing 116 of the IMD 104. In some examples, an array of electrodes on the housing 116 may be electrically connected to increase the area of electrode-tissue interface. The FF ventricular event morphology 314 of a unipolar far-field cardiac electrical signal may provide a global view of cardiac depolarization pattern, thus may improve accuracy of morphology-based capture verification. Due to the different conduction pathways involved and different conduction properties (e.g., velocity), His-bundle capture and myocardial capture may demonstrate different morphologies of the far-field cardiac electrical signal. The FF ventricular event-based capture detector 310 may extract from the sensed far-field ventricular depolarization one or more morphological features, such as an R wave width, a slope of the upstroke or down-stroke branch of the R wave, or an area under the curve of the FF-QRS or FFR wave, among others. In an example, a His-bundle His capture may be characterized by a narrower FF-QRS or FFR wave due to fast conduction and more coordinated contraction of the ventricles. A myocardial capture may be characterized by a wider FF-QRS or FFR wave due to relatively slower, cell-to-cell conduction, and less coordinated contraction of the ventricles. A width threshold may be programmed to a value such as to better distinguish slower, cell-to-cell myocardial response from faster His-bundle response. In an example, the width threshold is approximately 90-120 msec. In another example, the width threshold is approximately 120-140 msec. In an example, the width threshold may be at least partially automatically determined and dynamically updated based on patient historical HBP capture data, such as FF-QRS or FFR wave width for myocardial response and the FF-QRS or FFR wave width for His-bundle response.

Different capture status may result in different hemodynamic outcome. The hemodynamic sensor-based capture detector 320 may detect an increase in myocardial contractility in response to the delivery of the HBP pulses from the sensed hemodynamic signal, such as sensed by the sensing circuit 220. In an example, the physiologic sensor is a pressure sensor configured to sense cardiac pressure 322. The hemodynamic sensor-based capture detector 320 may detect the increase in myocardial contractility based on a rate of increase in the cardiac pressure. In another example, the physiologic sensor includes an impendence sensor configured to sense cardiac impedance 324. The hemodynamic sensor-based capture detector 320 may detect the increase in myocardial contractility based on a rate of increase in the cardiac impedance. The cardiac impedance may be measured by delivering high frequency subthreshold stimulation pulses, such as at approximately 20 Hz in an example. In an example, a volume plethysmography may be used to estimate cardiac contractility. In yet another example, the physiologic sensor is a heart sound sensor configured to sense heart sounds 326. The heart sound sensor may take the form of an accelerometer, an acoustic sensor, a microphone, a piezo-based sensor, or other vibrational or acoustic sensors. The accelerometer can be a two-axis or a three-axis accelerometer. Examples of the accelerometer may include flexible piezoelectric crystal (e.g., quartz) accelerometer or capacitive accelerometer, fabricated using micro electromechanical systems (MEMS) technology. One or more heart sound component, such as a first (S1), second (S2), third (S3), or fourth (S4) heart sound, may be detected from the heart sound signal. The hemodynamic sensor-based capture detector 320 may detect the increase in myocardial contractility based on a rate of increase in an intensity of the at least one heart sound component, or based on a rate of change in one or more HS-based cardiac timing intervals, such as a pre-ejection period (PEP), a systolic timing interval (STI), or a left-ventricular ejection time (LVET), among others. The detected increase in myocardial contractility may be compared to a threshold. A His-bundle capture is deemed to have occurred if the detected increase in myocardial contractility exceeds the threshold.

Figure 4A:
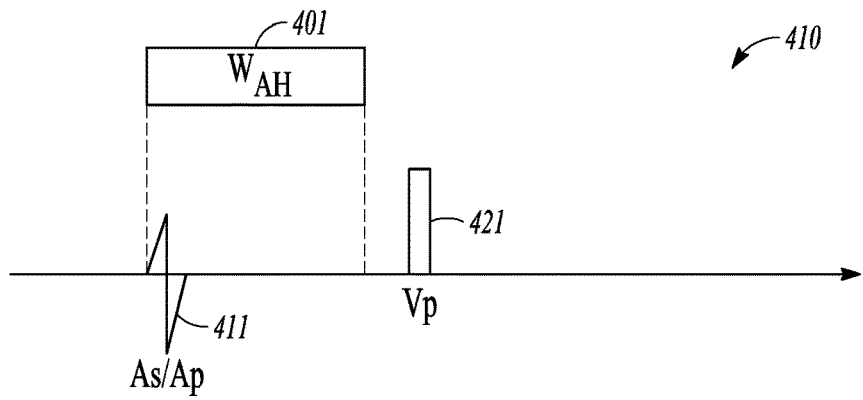
FIGS. 4A-C are diagrams illustrating examples of timing sequences and various detection windows for controlling delivery of HBP pulses and detection of correction of intra-Hisian block.
Figure 4B:
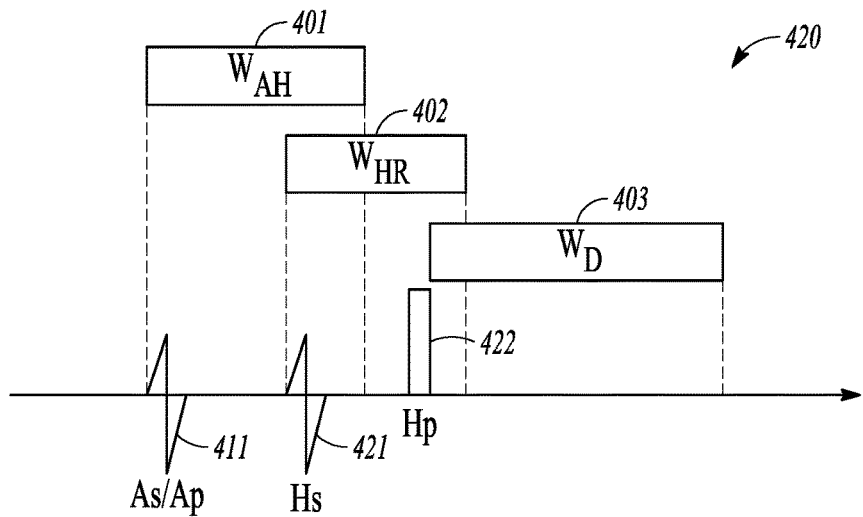
Figure 4C:
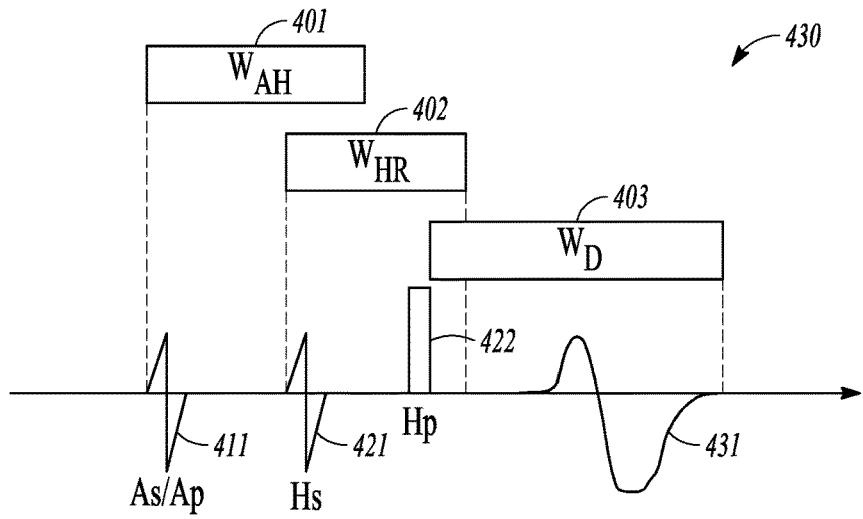

FIGS. 4A-C are diagrams 410, 420 and 430 each illustrating, by way of example, timing sequences and various detection windows for controlling delivery of HBP pulses and detection of correction of intra-Hisian block. The timing sequence and the detection results may be generated using the His-bundle pacing system 200. Some or all of the timing sequence and the detection results illustrated in FIGS. 4A-C, or variants thereof, may be displayed on a display screen of the user interface 240.

Diagram 410 in FIG. 4A illustrates an example where no intrinsic His-bundle activity (Hs) is detected following an intrinsic atrial event (As) or a paced atrial event (Ap). The As or Ap event may be detected using the sensing circuit 220. The detection of As or Ap event may trigger an atrio-Hisian (AH) window ($W_{AH}$) 401, and the timing circuit 239 may time the elapse of the $W_{AH}$. During the $W_{AH}$, the sensing circuit 220 may attempt to detect an intrinsic His-bundle activity. In the illustrated example 410, no intrinsic Hs event is detected within the $W_{AH}$. An absence of intrinsic His-bundle activity during the window $W_{AH}$ following the As or Ap event may indicate a low likelihood that the intra-Hisian block could be effectively corrected by delivery of HBP pulses. In the illustrated example, no HBP is attempted; instead, a ventricular pacing Vp may be delivered to one or both ventricles at a brief delay (Δ) after the expiration of $W_{AH}$. Examples of the ventricular pacing Vp may include RV pacing (at RV apex or free wall), CRT pacing, or multisite left ventricular pacing. In some examples, a high-output backup pacing may be delivered to elicit ventricular contraction and to prevent ventricular asystole. Although no HBP is attempted as illustrated in FIG. 4A, in some examples, a pilot HBP with higher stimulation energy may be attempted if no Hs was detected within the window $W_{AH}$. An absence of intrinsic Hs detection may also indicate that the conduction has been blocked upstream of the sensing electrode, such that an HBP may still be successful in recruiting the blocked fibers. If the pilot HBP fails to capture the His bundle and produce propagatable depolarization to the ventricles, alternative therapies may be delivered, such as direct ventricular pacing Vp, high-output pacing, or pacing from a separate electrode on the same lead or from those located on separate leads situated for RV and/or LV pacing.

Diagram 420 in FIG. 4B illustrates an example where an intrinsic His-bundle activity (Hs) 421 is detected within the window $W_{AH}$. The detection of the Hs event may trigger a His-bundle tissue refractory period ($W_{HR}$) 402. The timing circuit 239 may time the elapse of the $W_{HR}$, and time the delivery of an HBP pulse 422 within the refractory period $W_{HR}$. Because the portion of the intrinsically depolarized His tissue is still in its refractory period, it may not be responsive to the HBP pulse 422. However, if some other His tissue (e.g., previously latent conduction fibers in the His bundle) are excitable during $W_{HR}$, then the HBP pulse 422 may depolarize this other His tissue and produce propagation through the His-Purkinje conduction system, such that the intra-Hisian block may be corrected. As illustrated in FIG. 4B, the delivery of the HBP pulse 422 may trigger a capture detection window ($W_D$) 403. By way of example and not limitation, the capture detection window may have a duration of approximately 50-120 msec. The sensing circuit 220 may attempt to sense ventricular depolarization in response to the delivery of the HBP pulse 422, such as a FF-QRS or FFR wave at or near the His bundle or in the atrium. In the illustrated example, no FF-QRS or FFR wave is detected within the window $W_D$, suggesting no His-bundle capture and thus no correction of intra-Hisian block has occurred. One or more pacing parameters that control the generation and delivery of the HBP pulse 422 may be adjusted, and additional HBP pulses may be delivered according to the adjusted pacing parameters to attempt to correct the intra-Hisian block. Alternatively, ventricular pacing such as RV pacing, CRT pacing, or multisite pacing may be delivered in the absence of correction of intra-Hisian block.

Diagram 430 in FIG. 4C illustrates an example similar to the diagram 420, except that in this example the HBP pulse 422 captures the His bundle, and elicits ventricular depolarization, detected as a FF-QRS or FFR wave 431 within the capture detection window $W_D$. The FF-QRS or FFR wave 431, if meeting specific condition such as exceeding an intensity threshold, may indicate that the delivery of HBP pulse 422 has corrected the intra-Hisian block and produce myocardial contraction through the natural His-Purkinje conduction system.

Figure 5:
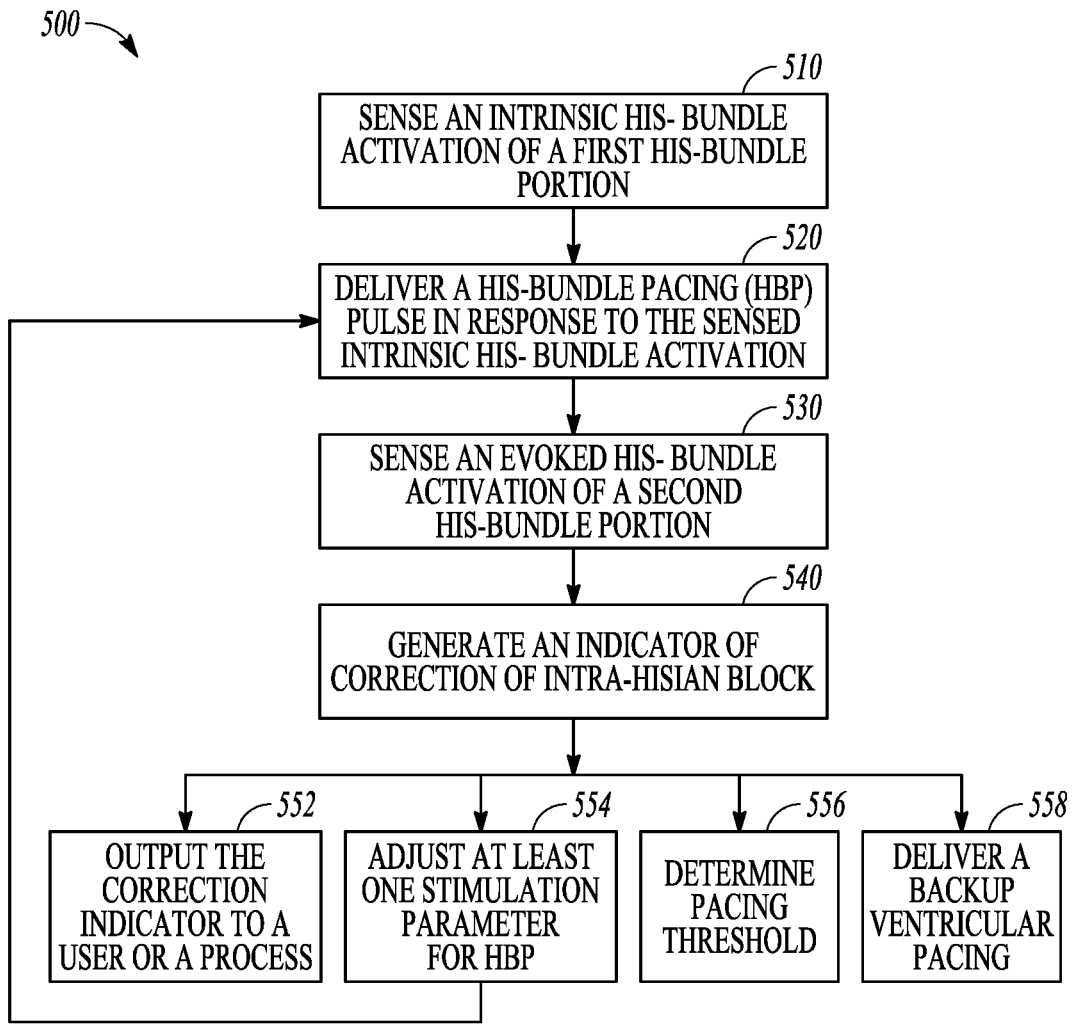
FIG. 5 illustrates generally an example of a method for providing His-bundle pacing to a patient having a cardiac conduction abnormality using a medical system.

FIG. 5 illustrates generally an example of a method 500 for proving His-bundle pacing to a patient having a cardiac conduction abnormality using a medical system. The method 500 may be implemented and executed in an ambulatory medical device such as an implantable or wearable medical device, or in a remote patient management system. In an example, the method 500 may be implemented in, and executed by, the IMD 104, one or more devices in the external system 140, or the His-bundle pacing system 200.

The method 500 commences at step 510, where an intrinsic His-bundle activation of at least a portion of the His-bundle tissue may be sensed, such as using the intrinsic His-bundle activation detector 222. The His-bundle activation may be confined to a first His-bundle portion, rather than the entire His bundle region. The intrinsic His-bundle activation may be detected from electrical or mechanical activity of a portion of the heart, such as using the intrinsic His-bundle activation detector 222 coupled to one or more electrodes or physiologic sensors. The intrinsic His-bundle activation may include an electrical signal representative of depolarization of the first His-bundle portion in response to a spontaneous sinus node firing (an "As" event) or in response to pacing at an atrium (an "Ap" event). In an example, the intrinsic His-bundle activation may be sensed within an atrio-Hisian (AH) window beginning at an As event or an Ap event in a cardiac cycle. FIGS. 4B and 4C illustrate examples where an intrinsic His-bundle activity (Hs) 421 is detected within an AH window $W_{AH}$ 401 following an As event or an Ap event.

At 520, a His-bundle pacing (HBP) pulse may be delivered to the His bundle region in response to the sensed intrinsic His-bundle activation. The HBP pulse may be generated from an electrostimulator, such as the electrostimulation circuit 210. The HBP pulse may be generated and delivered according to one or more pacing parameters of stimulation site, stimulation strength, stimulation mode, or stimulation timing, among other parameters. The stimulation site includes information about pacing site, pacing vector configuration (e.g., anode and cathode electrodes), or unipolar or bipolar pacing. The stimulation strength parameters determine the amount of energy delivered to the pacing site. The stimulation mode may include an atrial-Hisian (AH) pacing mode, a His-ventricular (HV) pacing mode, or an atrial-His-ventricular (AHV) pacing mode. The stimulation timing parameters determine the timing and sequence of pacing pulses. The HBP pulses may be delivered in multiple cardiac cycles.

The HBP pulse may be delivered subsequent to the detection of the intrinsic His-bundle activation (Hs). In an example, the HBP pulse may be delivered during a refractory period of the first portion of the intrinsically depolarized His-bundle tissue, such as the His-bundle tissue refractory period $W_{HR}$ 402 as illustrated in FIGS. 4B and 4C. As the intrinsically depolarized His tissue is still in the refractory period, it may not be responsive to the HBP pulse. However, some previously latent conduction fibers in the His bundle may be excitable during $W_{HR}$. The HBP pulse 422 may depolarize these fibers and produce propagation through the natural conduction system, and thus correct the intra-Hisian block.

At 530, an evoked His-bundle activation of a second His-bundle portion may be sensed following the delivery of the HBP pulse. The evoked His-bundle activation may be sensed from a physiological or hemodynamic signal indicative of tissue response to the delivery of HBP pulses. The evoked His-bundle activation may be sensed in a capture detection window triggered by the delivery of the HBP pulse, such as the capture detection window $W_D$ 403 illustrated in FIGS. 4B and 4C. Examples of the signal may include a ECG, a EGM of a portion of the heart such as atrial EGM, ventricular EGM, evoked His potential, an impedance signal, a heart sound signal, or a pressure signal, among others.

At 540, intra-Hisian block correction may be detected using the evoked His-bundle activation of the second His-bundle portion. An indicator of correction of intra-Hisian block may be generated if the block correction has occurred. The detection of intra-Hisian block correction may include a process of verifying capture status in response to the delivery of HBP pulses. The capture verification may be based on the sensed physiological or hemodynamic signal. Examples of capture verification methods are discussed below, such as with reference to FIGS. 6A-C.

In various examples, the capture verification at 540 may include detecting a His bundle capture directly resulting from the delivery of the HBP pulse, and myocardial capture directly resulting from the delivery of the HBP pulse. The capture status may further be classified as one of more capture types, including a selective His-bundle capture, a non-selective His-bundle capture, or a para-Hisian capture. The selective His-bundle capture refers to excitation (depolarization) of only the His bundle without excitation of the para-Hisian myocardium directly resulting from the HBP pulses. The non-selective His-bundle capture refers to excitation (depolarization) of both the His bundle and para-Hisian myocardium directly resulting from the HBP pulses. The para-Hisian capture refers to excitation (depolarization) of only the para-Hisian myocardium without excitation of the His bundle directly resulting from the HBP pulses. If neither the para-Hisian myocardium nor the His bundle is excited by the HBP pulses, then a loss of capture is indicated. Capture verification and capture type classification methods, such as described by commonly assigned U.S. Provisional Patent Application Ser. No. 62/580,711, entitled "SYSTEMS AND METHODS FOR HIS-BUNDLE PACING", filed on Nov. 2, 2017, are herein incorporated by reference in its entirety.

An indicator of correction of intra-Hisian block may be generated at 540 when the evoked His-bundle activation of the second His-bundle portion satisfies a specific condition. In an example, correction of intra-Hisian block is deemed to have occurred if a His-bundle capture is detected without myocardial capture (i.e., a selective His-bundle capture), or a His-bundle capture along with myocardial capture (i.e., a non-selective His-bundle capture). No correction of intra-Hisian block is deemed to have occurred if no His-bundle capture is detected within a specified evoked-response detection window. The first His-bundle portion may be a proximal His-bundle segment, and the second His-bundle portion may be a distal His-bundle segment. In an example, the first His-bundle portion includes right bundle fibers extending to a right bundle branch of the heart, and the second His-bundle portion includes left bundle fibers extending to a left bundle branch of the heart. In response to an intrinsic His-bundle activation at the first His-bundle portion, HBP pulses may be delivered, such as within the refractory period of the first His bundle. If His bundle capture is detected at least in the second His-bundle portion with or without myocardial capture, then an indicator of correction of an intra-Hisian left bundle branch block may be generated at 540.

The block correction indicator may be output to a user (e.g., a clinician) or a process at 552, such as being displayed on a display of the user interface 240. The sensed cardiac electrical signals and/or hemodynamic signals, the HBP, the detection results such as FF-QRS or FFR wave, or the programmed stimulation parameters, among other intermediate measurements or computations, may also be displayed. Additionally or alternatively, the block correction indicator may be used to adjust one or more stimulation parameters for generation or delivery of HBP at 554, such as via the parameter adjuster circuit 237. In some examples, stimulation parameter adjustment may be based on capture statistics computed using the capture verification results over multiple heart beats. Examples of the capture statistics may include percentages, histograms, or other measures of distribution of the selective His-bundle capture, non-selective His-bundle capture, or para-Hisian capture. The stimulation parameter adjustment may be performed when the capture statistics satisfy a specific condition. The parameter adjustment may include switching to a different stimulation site, using a different pacing vector configurations, adjusting the AH timing with respect to an intrinsic or paced atrial activation, adjusting stimulation strength such as one or more of pulse amplitude, pulse width, pulse frequency, pulse waveform, duty cycle, or stimulation duration. The HBP pulses may be generated and delivered at 520, according to the adjusted stimulation parameters to more effectively capture the His bundle, activate the natural conduction pathway, and improve patient cardiac performance.

At 556, the block correction indicator may additionally or alternatively be used to guide a pacing threshold test to determine a proper pacing threshold, such as by using the threshold test circuit 238. The pacing threshold represents minimal energy required to excite the His bundle. In an example, the pacing threshold test may be triggered when the tissue response to HBP pulses is classified as a loss of capture or a para-Hisian capture, in which no His bundle capture is achieved directly by the HBP pulses. Additionally or alternatively, the pacing threshold test may be carried out at the implant of the IMD 104, periodically at specified time period, or upon receiving a user command. The pacing threshold test may include delivering a series of HBP pulses with varying pulse amplitude, such as HBP pulses with decreasing amplitudes in a ramp-down test or HBP pulses with increasing amplitudes in a ramp-up test. Time intervals (e.g., HV intervals) between the delivery of HBP pulses and the corresponding sensed far-field ventricular activities (e.g., FF-QRS or FF R waves) may be measured. The pacing threshold may be determined as the pulse amplitude corresponding to a step change in the measured HV intervals, such as a step increase in the measured HV intervals in a ramp-down test. The step change in the HV intervals indicates a transition from a propagatable His-bundle excitation to a local para-Hisian myocardial excitation without His-bundle capture. In some other examples, the pacing threshold test may additionally be based on a change in morphology of far-field ventricular activities.

At 558, a backup pacing may be delivered if no correction of intra-Hisian block has occurred. The backup pacing may be delivered to a target ventricular site via a lead with associated electrodes disposed in or on a ventricle, such as a right ventricle. Examples of the backup pacing may include RV pacing, CRT pacing, BiV pacing, LV-only pacing, single site LV pacing, or multi-site LV pacing, among other pacing modalities delivered to improve myocardial contractility and cardiac performance. Additionally or alternatively, the backup pacing may be delivered at or near the His bundle. In an example, the backup pacing pulses include high-output pacing (HOP) pulses with higher pacing energy than conventional pacing pulses. In some examples, the HOP pulses may be delivered on an intermittent basis, such that the conventional pacing pulses are delivered in 3-5 cardiac cycles between the HOP pulses.

Figure 6A:
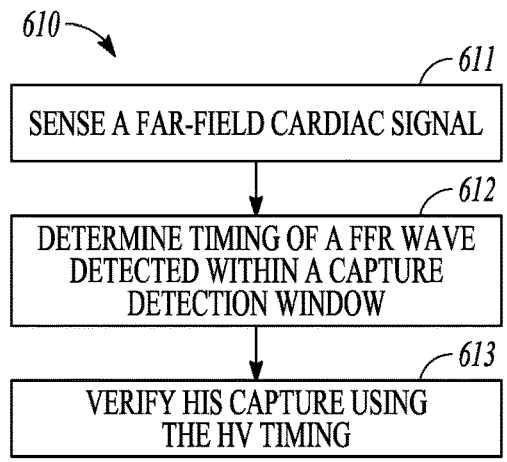
FIGS. 6A-C illustrate generally examples of methods of capture status verification using a far-field ventricular response or a hemodynamic sensor response to the delivery of HBP pulses.
Figure 6B:
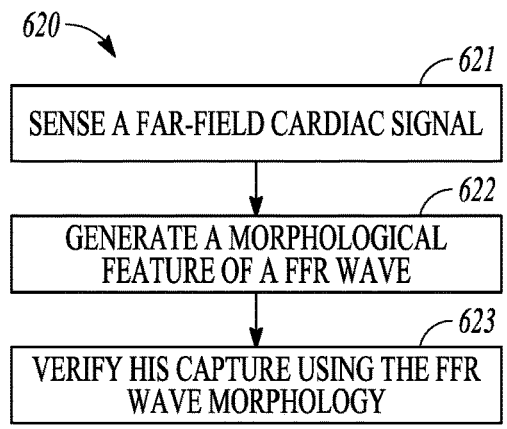
Figure 6C:
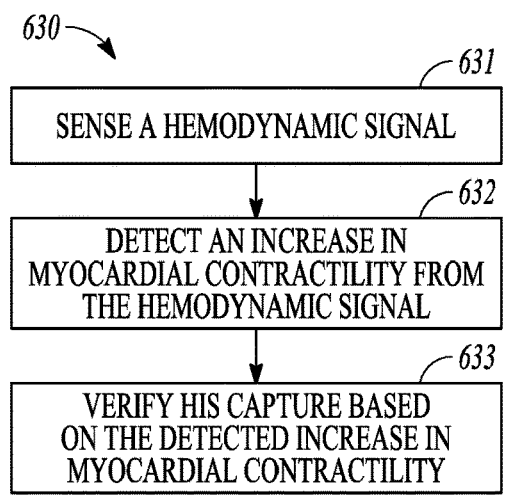

FIGS. 6A-C illustrate generally examples of methods 610, 620, and 630 of capture status verification using far-field (FF) ventricular activities or a hemodynamic sensor response to the delivery of HBP pulses. Each of the methods 610, 620, and 630 is an embodiment of at least a portion of the step 540 of the method 500, and can be implemented in, and executed by, the capture verification circuit 232.

FIG. 6A illustrates a method 610 of His-bundle capture verification based on timing of a far-field ventricular response to an HBP pulse. At 611 a far-field cardiac electrical signal may be sensed via one or more sensing electrodes disposed at or near the His bundle or in an atrium. In an example, the far-field cardiac electrical signal may be measured using a bipolar configuration including two electrodes disposed at or near the His bundle or in an atrium. At 612, FF-QRS or FFR waves may be detected from the FF cardiac electrical signal, such as within a capture detection window ($W_D$), as illustrated in FIG. 4C. Timing of the FF-QRS or FFR wave, if detected within the capture detection window, may be measured (referred to as HV timing) as an interval between the HBP pulse and the evoked FF-QRS or FFR wave. Generally, a His-bundle capture may be characterized by a shorter HV interval (measured from the delivery of an HBP pulse to the FF-QRS or FFR wave), due to relatively faster conduction of a depolarization wave through the natural conduction pathways. A myocardial capture may be characterized by a longer HV interval because of relatively slower, muscle-to-muscle conduction of the depolarization wave through the myocardium. At 613, His-bundle capture status may be determined using the HV timing. In an example, a bundle capture is declared if the HV interval falls below a specific threshold.

FIG. 6B illustrates a method 620 of His-bundle capture verification based on a morphology of far-field ventricular response to delivery of an HBP pulse. The method 620 begins at 621 to sense a far-field cardiac electrical signal, similar to step 611 of the method 610. At 622, one or more morphological features may be extracted from the FF-QRS or FFR wave. Unlike the method 610, which detects the timing of FF-QRS or FFR wave within the window $W_D$, detection of FF-QRS or FFR wave at 622 may not be limited within a time duration of the sensed cardiac electrical signal. An example of the morphological feature is a width of the sensed FF-QRS or FFR wave. Generally, a His-bundle capture may be characterized by a narrower FF-QRS or FFR wave due to relatively faster conduction through the natural conduction pathways. A myocardial capture may be characterized by a wider FF-QRS or FFR wave because of relatively slower conduction through the myocardium. Other examples of the morphological features may include a slope of the upstroke or down-stroke branch of the R wave, or an area under the curve of the FF-QRS or FFR wave, among others.

At 623, His-bundle capture status may be determined using the morphological feature of the FF-QRS or FFR wave. In an example, if the measured width the FF-QRS or FFR wave satisfies a specified condition such as falling below a width threshold, then a His-bundle response is deemed detected at 724. In an example, the width threshold is approximately 90-120 msec. In another example, the width threshold is approximately 120-140 msec. In various examples, the FF-QRS or FFR wave morphology may be compared to a morphology template, and a morphology similarity may be computed, such as using a distance measure or correlation between morphological features extracted respectively from the FF-QRS or FFR wave morphology and from the template. The His-bundle capture status may be determined based on the morphologic similarity.

FIG. 6C illustrates a method 630 of His-bundle capture verification based on a hemodynamic sensor response, such as using the hemodynamic sensor-based capture detector 320. The method 630 begins at 631 to sense a hemodynamic signal indicates an increase in myocardial contractility. Examples of the hemodynamic sensors may include cardiac pressure sensor, thoracic impedance sensor, or heart sound sensors, among others. At 632, an increase in myocardial contractility may be detected from the sensed hemodynamic signal. In an example, the increase in myocardial contractility may be based on a rate of increase in a cardiac pressure. In another example, the increase in myocardial contractility may be based on a rate of increase in the cardiac impedance. In yet another example, the increase in myocardial contractility may be based on a rate of increase in an intensity of the at least one heart sound component, or based on a rate of change in one or more HS-based cardiac timing intervals, such as a pre-ejection period (PEP), a systolic timing interval (STI), or a left-ventricular ejection time (LVET), among others. At 633, His-bundle capture status may be determined based on the detected increase in myocardial contractility. In an example, His-bundle capture is deemed to have occurred if the detected increase in myocardial contractility exceeds a threshold value.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code may form portions of computer program products. Further, the code can be tangibly stored on one or more volatile or non-volatile computer-readable media during execution or at other times.

The above detailed description is intended to be illustrative, and not restrictive. The scope of the disclosure should therefore be determined with references to the appended claims, along with the full scope of equivalents to which such claims are entitled.

What is claimed is:

1. A system for pacing a heart having a cardiac conduction abnormality, comprising:
   a sensing circuit configured to sense an intrinsic His bundle activation of a first His-bundle portion;
   an electrostimulation circuit configured to generate a His bundle pacing (HBP) pulse for delivery at or near the His bundle; and
   a control circuit, coupled to the electrostimulation circuit and the sensing circuit, configured to control the electrostimulation circuit to generate and deliver the HBP pulse according to one or more pacing parameters in response to the sensed intrinsic His bundle activation;
   wherein the control circuit includes a timing circuit configured to time the delivery of the HBP pulse within a tissue refractory period of the first His-bundle portion subsequent to the intrinsic His bundle activation.

2. The system of claim 1, wherein:
   the sensing circuit is electrically coupled to one or more electrodes disposed at or near the His bundle to sense the intrinsic His bundle activation of the first His-bundle portion; and
   the electrostimulation circuit is electrically coupled to the one or more electrodes disposed at or near the His bundle to deliver the HBP pulse.

3. The system of claim 1, wherein the sensing circuit is configured to sense the intrinsic His bundle activation within an atrio-Hisian time window beginning at a spontaneous atrial depolarization or an atrial pace event, and the control circuit is configured to control the electrostimulation circuit to generate and deliver the HBP pulse at or near the His bundle if the intrinsic His bundle activation is sensed within the atrio-Hisian time window.

4. The system of claim 2, wherein the control circuit is further configured to control the electrostimulation circuit to generate and deliver a ventricular pacing pulse to a ventricle if no intrinsic His bundle activation is sensed within the atrio-Hisian time window.

5. The system of claim 1, wherein:
   the sensing circuit is further configured to sense an evoked His bundle activation of a second His-bundle portion in response to the delivery of the HBP pulse; and
   the control circuit is configured to generate an indicator of correction of intra-Hisian block when the evoked His bundle activation of the second His-bundle portion satisfies a specific condition.

6. The system of claim 5, wherein the first His-bundle portion includes right bundle fibers extending to a right bundle branch of the heart, and the second His-bundle portion includes left bundle fibers extending to a left bundle branch of the heart, and
   wherein the control circuit is configured to generate the indicator of correction of an intra-Hisian left bundle branch block when the evoked His bundle activation of the left bundle branch fibers satisfies a specific condition.

7. The system of claim 5, wherein the sensing circuit is configured to sense the evoked His bundle activation including a far-field R wave in response to the delivery of HBP pulse.

8. The system of claim 5, comprising a physiologic sensor configured to sense a hemodynamic signal, wherein the sensing circuit is configured to sense the evoked His bundle activation including to detect an increase in myocardial contractility from the sensed hemodynamic signal.

9. The system of claim 5, wherein:
   the control circuit includes a parameter adjuster circuit configured to adjust at least one of the one or more pacing parameters if the evoked His bundle activation of the second His-bundle portion indicates no correction of intra-Hisian block; and
   the electrostimulation circuit is configured to generate the HBP pulse for delivery at or near the His bundle according to the adjusted at least one pacing parameter.

10. The system of claim 1, wherein the control circuit includes a threshold test circuit configured to determine an individualized pacing threshold representing minimal energy to excite the His bundle and to correct the cardiac conduction abnormality, and the electrostimulation circuit is configured to generate an HBP above the pacing threshold for delivery at or near the His bundle.

11. The system of claim 10, wherein:
the electrostimulation circuit is configured to generate and deliver HBP pulse at or near the His bundle according to a pacing parameter programmed to a plurality of values;
the sensing circuit is configured to sense respective far-field R waves in response to the delivery of HBP pulse; and
the threshold test circuit is configured to determine the pacing threshold based on a step change in time intervals between the delivery of HBP pulse and the sensed respective far-field R waves.

12. The system of claim 1, wherein the control circuit includes a pacing site selector circuit configured to determine a target His bundle pacing site for delivering the HBP pulse based on evoked His bundle activations in response to HBP pulse delivered at each of a plurality of candidate His bundle sites.

13. The system of claim 12, wherein the evoked His bundle activations include far-field R waves in response to the delivery of the HBP pulse, and the pacing site selector circuit is configured to determine the target His bundle pacing site based on measurements of width of the sensed far-field R waves.

14. The system of claim 12, wherein the evoked His bundle activations include hemodynamic signals in response to the delivery of the HBP pulse, and the pacing site selector circuit is configured to determine the target His bundle pacing site based on the sensed hemodynamic signals.

15. A method for pacing a heart having a cardiac conduction abnormality using a cardiac pacing system, the method comprising:
sensing an intrinsic His bundle activation of a first His-bundle portion using a sensing circuit; and
under a control of a control circuit, delivering a His bundle pacing (HBP) pulse according to one or more pacing parameters in response to the sensed intrinsic His bundle activation, the HBP pulse generated using an electrostimulation circuit;
wherein delivering the HBP pulse includes timing the delivery of the HBP pulse within a tissue refractory period of the first His-bundle portion subsequent to the intrinsic His bundle activation.

16. The method of claim 15, comprising:
sensing an evoked His bundle activation of a second His-bundle portion using the sensing circuit in response to the delivery of the HBP pulse; and
generating an indicator of correction of intra-Hisian block when the evoked His bundle activation of the second His-bundle portion satisfies a specific condition.

17. The method of claim 16, wherein the first His-bundle portion includes right bundle fibers extending to a right bundle branch of the heart, and the second His-bundle portion includes left bundle fibers extending to a left bundle branch of the heart, and
wherein generating the indicator of correction includes generating an indicator of correction of an intra-Hisian left bundle branch block when the evoked His bundle activation of the left bundle branch fibers satisfies a specific condition.

18. The method of claim 16, wherein sensing the evoked His bundle activation includes sensing a far-field R wave in response to the delivery of HBP pulse.

19. The method of claim 16, wherein sensing the evoked His bundle activation includes sensing a hemodynamic signal and detecting an increase in myocardial contractility from the sensed hemodynamic signal.

20. The method of claim 16, further comprising:
adjusting at least one of the one or more pacing parameters if the evoked His bundle activation of the second His-bundle portion indicates no correction of intra-Hisian block; and
generating the HBP pulse for delivery at or near the His bundle according to the adjusted at least one pacing parameter.

* * * * *